US008895818B2

(12) United States Patent
Chomet et al.

(10) Patent No.: US 8,895,818 B2
(45) Date of Patent: Nov. 25, 2014

(54) TRANSGENIC PLANTS WITH ENHANCED AGRONOMIC TRAITS

(75) Inventors: Paul S. Chomet, Mystic, CT (US); Donald C. Anstrom, Pawcatuck, CT (US); Jacqueline E. Heard, Stonington, CT (US); Adrian Lund, Halstead, KS (US); Jill Deikman, Davis, CA (US)

(73) Assignee: Monsanto Technology LLC, St. Louis, MO (US)

( * ) Notice: Subject to any disclaimer, the term of this patent is extended or adjusted under 35 U.S.C. 154(b) by 1845 days.

(21) Appl. No.: 11/311,920

(22) Filed: Dec. 19, 2005

(65) Prior Publication Data

US 2006/0179511 A1 Aug. 10, 2006

Related U.S. Application Data

(60) Provisional application No. 60/638,099, filed on Dec. 21, 2004.

(51) Int. Cl.
*A01H 5/00* (2006.01)
*A01H 5/10* (2006.01)
*C12N 15/82* (2006.01)
*C07K 14/415* (2006.01)

(52) U.S. Cl.
CPC .......... *C07K 14/415* (2013.01); *C12N 15/8251* (2013.01); *C12N 15/8274* (2013.01); *C12N 15/8261* (2013.01); *C12N 15/8271* (2013.01); *C12N 15/8247* (2013.01); *C12N 15/8275* (2013.01); *C12N 15/8273* (2013.01)
USPC .......... 800/320.1; 435/419; 435/468; 800/295

(58) Field of Classification Search
None
See application file for complete search history.

(56) References Cited

U.S. PATENT DOCUMENTS

| | | | |
|---|---|---|---|
| 6,399,861 | B1 | 6/2002 | Anderson et al. |
| 6,417,428 | B1 | 7/2002 | Thomashow et al. |
| 6,777,589 | B1 | 8/2004 | Lundquist et al. |
| 7,135,616 | B2 | 11/2006 | Heard et al. |
| 7,511,190 | B2 | 3/2009 | Creelman et al. |
| 2004/0019925 | A1 | 1/2004 | Heard et al. |
| 2004/0019927 | A1 | 1/2004 | Sherman et al. ............... 800/289 |
| 2009/0158452 | A1 | 6/2009 | Johnson et al. |
| 2010/0083402 | A1 | 4/2010 | Heard et al. |

FOREIGN PATENT DOCUMENTS

| | | | |
|---|---|---|---|
| WO | WO 02/15675 | | 2/2002 |
| WO | WO 02 15675 | * | 2/2002 |
| WO | WO 02/16655 | | 2/2002 |
| WO | WO0215675 A1 | * | 2/2002 |
| WO | WO 03/013227 | * | 2/2003 |
| WO | WO 03/013228 | | 2/2003 |
| WO | WO 03/013228 A2 | * | 2/2003 |
| WO | WO03013227 A2 | * | 2/2003 |
| WO | WO 2006/130156 | | 12/2006 |

OTHER PUBLICATIONS

Collins et al. (The Plant Cell, 11:1365-1376, Jul. 1999).*
Nishimura et al. (Plant Cell Physiol., 41(5):583-590, 2000).*
Uberlacker et al. (The Plant Cell, 8:349-362, 1996).*
Sentoku et al. (Developmental Biology, 220:358-364, 2000).*
Wells, Biochemistry 29:8509-8517, 1990.*
Ngo et al., (The Protein Folding Problem and Tertiary Structure Prediction, K. Merz., and S. Le Grand (eds.) pp. 492-495,1994).*
Guo et al. (PNAS, 101: 9205-9210, 2004).*
Keskin et al. (Protein Science, 13:1043-1055, 2004).*
Thornton et al. (Nature structural Biology, structural genomics supplement, Nov. 2000).*
Lall et al., Genetics 167:1883 2004.*
Whisstock_Q Rev Biophys_36_307_2003.*
Lazar et al_Mol Cell Biol 8_1247_1988.*
Sakakibara et al., "Isolation of homeodomain-leucine zipper genes from the moss *Physcomitrella patens* and the evolution of homeodomain-leucine zipper-genes in land plants," *Molecular Biology and Evolution*, 18(4):491-502, 2001.
Schena et al., "The HAT4 gene of *Arabidopsis* encodes a developmental regulator," *Genes and Development*, 7(3):367-379, 1993.
Eddy, "Profile hidden Markov models," *BioInformatics Rev.*, 14(9):755-763, 1998.
GenBank Accession No. AC005560, dated Mar. 11, 2002.
GenBank Database Accession No. AF145727, dated Mar. 17, 2000.
GenBank Database Accession No. AJ31181, dated Apr. 22, 2008.
GenBank Database Accession No. EU966190, dated Dec. 10, 2008.
GenBank Database Accession No. NM_001050228, dated Feb. 14, 2008.
GenBank Database Accession No. NM_126204, dated May 22, 2008.
GenPept Database Accession No. AAC67320, dated Mar. 11, 2002.
GenPept Database Accession No. ACG38308, dated Dec. 10, 2008.
GenPept Database Accession No. EAY75147, dated Dec. 17, 2008.
GenPept Database Accession No. NP_001043693, dated Feb. 14, 2008.
GenPept Database Accession No. NP_178252, dated May 22, 2008.
Declaration Under 37 C.F.R. § 1.132 of Paul Loida regarding U.S. Appl. No. 11/311,920, dated Aug. 30, 2010.
U.S. Appl. No. 09/713,994, Keddie et al.

(Continued)

*Primary Examiner* — Vinod Kumar
*Assistant Examiner* — Russell Boggs
(74) *Attorney, Agent, or Firm* — Dentons US LLP; David Lanzotti, Esq.

(57) ABSTRACT

This disclosure describes screening a population of transgenic plants derived from plant cells transformed with recombinant DNA for expression of proteins with homeobox domains to identify plant cells of specific transgenic events that are useful for imparting enhanced traits to transgenic crop plants. Traits include enhanced nitrogen use efficiency, increased yield, enhanced water use efficiency, enhanced tolerance to cold stress and/or improved seed compositions. Also disclosed are transgenic seeds for growing a transgenic plant having the recombinant DNA in its genome and exhibiting the screened enhance trait. Also disclosed are methods for generating seed and plants based on the transgenic events.

12 Claims, No Drawings

(56) References Cited

OTHER PUBLICATIONS

Aso et al., "Characterization of Homeodomain-Leucine Zipper Genes in the Fern *Ceratopteris richardii* and the Evolution of the Homeodomain-Leucine Zipper Gene Family in Vascular Plants"; *Mol. Biol. Evol.* 16(4):544-552: 1999.
Cao et al., "The *Arabidopsis* NPR1 Gene That Controls Systemic Acquired Resistance Encodes a Novel Protein Containing Ankyrin Repeats," *Cell* 88:57-63; Jan. 1997.
Genbank Accession No. H76651; submitted Jan. 5, 1998.
Larkin at al., "Roles of the GLABROUS1 and *TRANSPARENT TESTA* GLABRA Genes in *Arabidopsis* Trichome Development," *The Plant Cell* 6:1065-1076; 1994.
Lin et al., "Sequence and analysis of chromosome 2 of the plant *Arabidopsis thaliana*";*Nature*; 402:761-768; 1999.
Liu et al., Two Transcription Factors, DREB1 and DREB2, with an EREBP/AP2 DNA binding domain separate two cellular signal transduction pathways in drought- and low-temperature- responsive gene expressing respectively, in *Arabidopsis. The Plant Cell.* Aug 10(8);1391-406; 1998.
Meijer et al., "HD-Zip proteins of families I and II from rice interactions and functional properties"; *Molecular and General Genetics*; 263:12-21; 2000.
NCBI Protein Sequence Accession No. Q8S9N6, Natl Lib of Medicine, NIH, Bethesda, MD, Submitted Feb. 19, 2014.
Newman at a/,"Genes galore: a summary of methods for accessing results from large-scale partial sequencing of anonymous *Arabidopsis* cDNA clones," *Plant Physiology* 106:1241-1255; 1994.
Riechmann et al., "*Arabidopsis* transcription factors: genome-wide comparative analysis among eukaryotes," *Science*; 290:2105-2110; 2000.
Ruberti et al., "A novel class of plant proteins containing a homeodomain with a closely linked leucine zipper motif," *EMBO J.* Jul:10(7); 1789-91; 1991.
Schena et al., "Structure of homeobox-leucine zipper genes suggests a model for the evolution of gene families"; *Proc Natl Acad Sci USA*; 91:8393-8397; 1994.
USPTO; Advisory Action for U.S. Appl. No. 10/374,780 dated Sep. 11, 2008.
Response to Office Action for U.S. Appl. No. 10/374,780 dated Sep. 10, 2008.
Uspto; Advisory Action for U.S. Appl. No. 10/374,780 dated Jul. 21, 2008.
Response after Final for U.S. Appl. No. 10/374,780 dated Jul. 2, 2008.
Declaration of Gregory Nadzan for U.S. Appl. No. 10/374,780 dated Jul. 2, 2008.
USPTO; Final Rejection for U.S. Appl. No. 10/374,780 dated Apr. 2, 2008.
Supplemental Response to Office Action for U.S. Appl. No. 10/374,780 dated Jan. 3, 2008.
Response to Office Action for U.S. Appl. No. 10/374,780 dated Nov. 29, 2007.
USPTO; Non-final Office Action for U.S. Appl. No. 10/374,780 dated Jun. 29, 2007.
Response to Office Action for U.S. Appl. No. 10/374,780 dated Apr. 3, 2007.
Declaration of Rebecca L. Thompson-Mize for U.S. Appl. No. 10/374,780 dated Apr. 3, 2007.
USPTO; Non-final Office Action for U.S. Appl. No. 10/374,780 dated Nov. 30, 2006.
Response to Office Action for U.S. Appl. No. 10/374,780 dated Sep. 11, 2006.
USPTO; Non-final Office Action for U.S. Appl. No. 10/374,780 dated Apr. 7, 2006.
Response to Office Action for U.S. Appl. No. 12/573,311 dated Jun. 7, 2013.
USPTO; Final Rejection for U.S. Appl. No. 12/573,311 dated Dec. 7, 2012.
Declaration of Paul Loida for U.S. Appl. No. 12/573,311 dated Sep. 4, 2012.
Declaration of Elena Rice for U.S. Appl. No. 12/573,311 dated Sep. 4, 2012.
Response to Office Action for U.S. Appl. No. 12/573,311 dated Sep. 4, 2012.
USPTO; Non-final Office Action for U.S. Appl. No. 12/573,311 dated Mar. 1, 2012.
USPTO; Final Rejection for U.S. Appl. No. 09/713,994 dated Jan. 30, 2006.
Response to Office Action for U.S. Appl. No. 09/713,994 dated Nov. 7, 2005.
USPTO; Non-final Office Action for U.S. Appl. No. 09/713,994 dated Jul. 14, 2005.
Response to Office Action for U.S. Appl. No. 09/713,994 dated Apr. 20, 2005.
Response to Office Action for U.S. Appl. No. 09/713,994 dated Mar. 31, 2003.
USPTO; Non-final Office Action for U.S. Appl. No. 09/713,994 dated Jul. 30, 2002.
Canadian Intellectual Property Office; Office Action for Application No. 2,456,979 dated May 2, 2011.
Response to Office Action for Application No. 2,456,979 dated Nov. 1, 2011.
Canadian Intellectual Property Office; Office Action for Application No. 2,456,979 dated Apr. 10, 2012.
Response to Office Action for Application No. 2,456,979 dated Oct. 10, 2012.
Canadian Intellectual Property Office; Office Action for Application No. 2,456,979 dated Apr. 9, 2013.
Response to Office Action for Application No. 2,456,979 dated Sep. 24, 2013.
Canadian Intellectual Property Office; Notice of Allowance for Application No. 2,456,979 dated Oct. 22, 2013.
Canadian Intellectual Property Office; Office Action for Application No. 2,573,987 dated Feb. 13, 2012.
Response to Office Action Application No. 2,573,987 dated Aug. 13, 2012.
Canadian Intellectual Property Office; Office Action for Application No. 2,573,987 dated Jan. 23, 2013.

* cited by examiner

SEQUENCE LISTING

```
<160> NUMBER OF SEQ ID NOS: 15

<210> SEQ ID NO 1
<211> LENGTH: 828
<212> TYPE: DNA
<213> ORGANISM: Arabidopsis thaliana

<400> SEQUENCE: 1
atgataaaac tactatttac gtacatatgc acatacacat ataaactata tgctctatat      60
catatggatt acgcatgcgt gtgtatgtat aaatataaag gcatcgtcac gcttcaagtt     120
tgtctctttt atattaaact gagagttttc ctctcaaact ttaccttttc ttcttcgatc     180
ctagctctta agaaccctaa taattcattg atcaaaataa tggcgatttt gccggaaaac     240
```

```
tcttcaaact tggatcttac tatctccgtt ccaggcttct cttcatcccc tctctccgat    300
gaaggaagtg gcggaggaag agaccagcta aggctagaca tgaatcggtt accgtcgtct    360
gaagacggag acgatgaaga attcagtcac gatgatggct ctgctcctcc gcgaaagaaa    420
ctccgtctaa ccagagaaca gtcacgtctt cttgaagata gtttcagaca gaatcatacc    480
cttaatccca acaaaagga agtacttgcc aagcatttga tgctacggcc aagacaaatt    540
gaagtttggt ttcaaaaccg tagagcaagg agcaaattga agcaaaccga gatggaatgc    600
gagtatctca aaaggtggtt tggttcatta acggaagaaa accacaggct ccatagagaa    660
gtagaagagc ttagagccat aaaggttggc ccaacaacgg tgaactctgc ctcgagcctt    720
actatgtgtc ctcgctgcga gcgagttacc cctgccgcga gcccttcgag ggcggtggtg    780
ccggttccgg ctaagaaaac gtttccgccg caagagcgtg atcgttga                 828
```

<210> SEQ ID NO 2
<211> LENGTH: 678
<212> TYPE: DNA
<213> ORGANISM: Zea mays

<400> SEQUENCE: 2

```
atggggtcca cttctccttc aggcctggag ctcaccatgg ctgtcccggg cctcagctcc     60
tcctctggct cagaggggtt tggatgcaac aacaacaacg ggagcgggaa cggaacaac    120 atgagggacc tggacatgaa ccagccggcg agcggcggcg aggaggagga gttcccaatg    180
gggagcgtgg aggaggagga ggacgagcgc ggcggcgccg gcgggccgca ccgcgccaag    240
aagctccggc tgtccaagga gcagtcccgc ctcctggagg agagcttccg cctcaaccac    300
accctcacac cgaagcaaaa ggaggccttg gctgtcaagc tcaagctgcg gcccaggcag    360
gtggaggtct ggttccagaa ccgcagggct aggacgaagc ttaagcagac ggagctggag    420
tgcgagtacc tgaagcgctg cttcggctcg ctgaccgagg agaaccggcg gctgcagcgg    480
gaggtggagg agctgcgcgc gatgcgggtg gccccgccca ccgtgctctc cccgcacacc    540
cggcagccgc tcccggcgtc cgcgctcacc atgtgcccgc gctgcgagcg catcaccgcc    600
gcaacggccg cgcgcacccc acgcccgccg cccgccgcga cccctcca cccgcgccgc    660 ccgtccgcgg cgttttag                                                  678
```

<210> SEQ ID NO 3
<211> LENGTH: 642
<212> TYPE: DNA
<213> ORGANISM: Glycine max

<400> SEQUENCE: 3

```
atggcggttt taccaagtag ctcctcaagc ttggaattga ccatatctgt acctggtttt     60
gcttcttcac caacccttct tccctcatca tctgtgaaag aattggacat aaatcaagta    120
cctcttgaag aagattggat ggcatcaaac atggaagatg aagaagaaag cagcaatgga    180
gaacctcctc gaaagaaact ccgtctcaca aaggaacaat ctcttctcct tgaagaaagc    240
tttagacaaa accacacgtt gaacccaaag cagaaagagt cttggcaat gcaactgaag    300 ctgcgaccaa gcaagtggga ggtgtggttt cagaaccgta gggccaggag caagctgaag    360
cagacagaga tggagtgcga gtacctcaag aggtggttcg gttccctcac agagcagaac    420
cggaggctcc agaggaagt ggaggagctg cgagccatta aggtgggccc acccaccgtg    480
atctcccctc actcctgcga accgtccccg gcctccacac tttccatgtg tcccgctgc    540 gagcgtgtca cctccaccgc cgacaaaccg ccctccgccg cggccacttt gtccgctaaa    600
```

```
gtgccgccaa ctcaatcccg ccaaccctcc gcggcctgtt ag                      642
```

<210> SEQ ID NO 4
<211> LENGTH: 690
<212> TYPE: DNA
<213> ORGANISM: Oryza sativa

<400> SEQUENCE: 4

```
atgatgggggg ccacttctcc gtcaggcctg gagctcacca tggctgtccc cggcctcagc    60
tcctctggtt cagaaggggc cggttgcaac aacaacaacg ccggtggcgg ctgcaacatg   120
agggacctgg acatcaacca gccggcgagc ggcggcgagg aggaggagtt cccgatgggc   180
agcgtggagg aggacgagga ggagaggggc gtcggtgggc cccaccgccc caagaagctc   240
cgcctctcca aggagcagtc ccgcctcctc gaggagagct ccgcctcaa ccatacccctc   300
acgccgaagc aaaaggaggc cttggcgatc aaactgaagc tgcggccgag gcaggtggag   360
gtctggtttc agaaccgtag ggcaaggacg aagctgaagc agacggagat ggagtgcgag   420
tacctgaagc gctgcttcgg gtcgctgacg gaggagaacc gccggctgca gcgggaggtg   480
gaggagctgc gggcgatgcg ggtggccccg cccacggtgc tctcgccgca caccaggcag   540
ccgctcccgg cgtccgcgct caccatgtgc ccccgctgcg agcgcatcac cgccgccacc   600
ggcccgcctg ccgtgcgccc gccgccgtcg tcagccgccg ccgccgcccc ctcgcccttc   660
caccctcgcc gcccctctgc ggccttctag                                   690
```

<210> SEQ ID NO 5
<211> LENGTH: 275
<212> TYPE: PRT
<213> ORGANISM: Arabidopsis thaliana

<400> SEQUENCE: 5

```
Met Ile Lys Leu Leu Phe Thr Tyr Ile Cys Thr Tyr Thr Tyr Lys Leu
1               5                   10                  15

Tyr Ala Leu Tyr His Met Asp Tyr Ala Cys Val Cys Met Tyr Lys Tyr
            20                  25                  30

Lys Gly Ile Val Thr Leu Gln Val Cys Leu Phe Tyr Ile Lys Leu Arg
        35                  40                  45

Val Phe Leu Ser Asn Phe Thr Phe Ser Ser Ser Ile Leu Ala Leu Lys
    50                  55                  60

Asn Pro Asn Asn Ser Leu Ile Lys Ile Met Ala Ile Leu Pro Glu Asn
65                  70                  75                  80

Ser Ser Asn Leu Asp Leu Thr Ile Ser Val Pro Gly Phe Ser Ser Ser
                85                  90                  95

Pro Leu Ser Asp Glu Gly Ser Gly Gly Gly Arg Asp Gln Leu Arg Leu
            100                 105                 110

Asp Met Asn Arg Leu Pro Ser Ser Glu Asp Gly Asp Glu Glu Phe
        115                 120                 125

Ser His Asp Asp Gly Ser Ala Pro Pro Arg Lys Lys Leu Arg Leu Thr
    130                 135                 140

Arg Glu Gln Ser Arg Leu Leu Glu Asp Ser Phe Arg Gln Asn His Thr
145                 150                 155                 160

Leu Asn Pro Lys Gln Lys Glu Val Leu Ala Lys His Leu Met Leu Arg
                165                 170                 175

Pro Arg Gln Ile Glu Val Trp Phe Gln Asn Arg Arg Ala Arg Ser Lys
            180                 185                 190
```

Leu Lys Gln Thr Glu Met Glu Cys Glu Tyr Leu Lys Arg Trp Phe Gly
            195                 200                 205

Ser Leu Thr Glu Glu Asn His Arg Leu His Arg Glu Val Glu Glu Leu
    210                 215                 220

Arg Ala Ile Lys Val Gly Pro Thr Thr Val Asn Ser Ala Ser Ser Leu
225                 230                 235                 240

Thr Met Cys Pro Arg Cys Glu Arg Val Thr Pro Ala Ala Ser Pro Ser
            245                 250                 255

Arg Ala Val Val Pro Val Pro Ala Lys Lys Thr Phe Pro Pro Gln Glu
                260                 265                 270

Arg Asp Arg
        275

<210> SEQ ID NO 6
<211> LENGTH: 225
<212> TYPE: PRT
<213> ORGANISM: Zea mays

<400> SEQUENCE: 6

Met Gly Ser Thr Ser Pro Ser Gly Leu Glu Leu Thr Met Ala Val Pro
1               5                   10                  15

Gly Leu Ser Ser Ser Gly Ser Glu Gly Phe Gly Cys Asn Asn Asn
            20                  25                  30

Asn Gly Ser Gly Asn Gly Asn Asn Met Arg Asp Leu Asp Met Asn Gln
            35                  40                  45

Pro Ala Ser Gly Gly Glu Glu Glu Phe Pro Met Gly Ser Val Glu
    50                  55                  60

Glu Glu Glu Asp Glu Arg Gly Gly Ala Gly Gly Pro His Arg Ala Lys
65                  70                  75                  80

Lys Leu Arg Leu Ser Lys Glu Gln Ser Arg Leu Leu Glu Glu Ser Phe
                85                  90                  95

Arg Leu Asn His Thr Leu Thr Pro Lys Gln Lys Glu Ala Leu Ala Val
            100                 105                 110

Lys Leu Lys Leu Arg Pro Arg Gln Val Glu Val Trp Phe Gln Asn Arg
        115                 120                 125

Arg Ala Arg Thr Lys Leu Lys Gln Thr Glu Leu Glu Cys Glu Tyr Leu
    130                 135                 140

Lys Arg Cys Phe Gly Ser Leu Thr Glu Glu Asn Arg Arg Leu Gln Arg
145                 150                 155                 160

Glu Val Glu Glu Leu Arg Ala Met Arg Val Ala Pro Pro Thr Val Leu
                165                 170                 175

Ser Pro His Thr Arg Gln Pro Leu Pro Ala Ser Ala Leu Thr Met Cys
            180                 185                 190

Pro Arg Cys Glu Arg Ile Thr Ala Ala Thr Ala Ala Thr Pro Arg
        195                 200                 205

Pro Pro Pro Ala Ala Ser Pro Phe His Pro Arg Arg Pro Ser Ala Ala
    210                 215                 220

Phe
225

<210> SEQ ID NO 7
<211> LENGTH: 213
<212> TYPE: PRT
<213> ORGANISM: Glycine max

<400> SEQUENCE: 7

```
Met Ala Val Leu Pro Ser Ser Ser Ser Leu Glu Leu Thr Ile Ser
1               5                   10                  15

Val Pro Gly Phe Ala Ser Ser Pro Thr Leu Leu Pro Ser Ser Val
                20                  25                  30

Lys Glu Leu Asp Ile Asn Gln Val Pro Leu Glu Glu Asp Trp Met Ala
            35                  40                  45

Ser Asn Met Glu Asp Glu Glu Ser Ser Asn Gly Glu Pro Pro Arg
    50                  55                  60

Lys Lys Leu Arg Leu Thr Lys Glu Gln Ser Leu Leu Glu Glu Ser
65                  70                  75                  80

Phe Arg Gln Asn His Thr Leu Asn Pro Lys Gln Lys Glu Ser Leu Ala
                85                  90                  95

Met Gln Leu Lys Leu Arg Pro Arg Gln Val Glu Val Trp Phe Gln Asn
            100                 105                 110

Arg Arg Ala Arg Ser Lys Leu Lys Gln Thr Glu Met Glu Cys Glu Tyr
            115                 120                 125

Leu Lys Arg Trp Phe Gly Ser Leu Thr Glu Gln Asn Arg Arg Leu Gln
            130                 135                 140

Arg Glu Val Glu Glu Leu Arg Ala Ile Lys Val Gly Pro Pro Thr Val
145                 150                 155                 160

Ile Ser Pro His Ser Cys Glu Pro Leu Pro Ala Ser Thr Leu Ser Met
                165                 170                 175

Cys Pro Arg Cys Glu Arg Val Thr Ser Thr Ala Asp Lys Pro Pro Ser
            180                 185                 190

Ala Ala Ala Thr Leu Ser Ala Lys Val Pro Pro Thr Gln Ser Arg Gln
            195                 200                 205

Pro Ser Ala Ala Cys
        210

<210> SEQ ID NO 8
<211> LENGTH: 229
<212> TYPE: PRT
<213> ORGANISM: Oryza sativa

<400> SEQUENCE: 8

Met Met Gly Ala Thr Ser Pro Ser Gly Leu Glu Leu Thr Met Ala Val
1               5                   10                  15

Pro Gly Leu Ser Ser Ser Gly Ser Glu Gly Ala Gly Cys Asn Asn Asn
                20                  25                  30

Asn Ala Gly Gly Gly Cys Asn Met Arg Asp Leu Asp Ile Asn Gln Pro
            35                  40                  45

Ala Ser Gly Gly Glu Glu Glu Phe Pro Met Gly Ser Val Glu Glu
    50                  55                  60

Asp Glu Glu Glu Arg Gly Val Gly Gly Pro His Arg Pro Lys Lys Leu
65                  70                  75                  80

Arg Leu Ser Lys Glu Gln Ser Arg Leu Leu Glu Glu Ser Phe Arg Leu
                85                  90                  95

Asn His Thr Leu Thr Pro Lys Gln Lys Glu Ala Leu Ala Ile Lys Leu
            100                 105                 110

Lys Leu Arg Pro Arg Gln Val Glu Val Trp Phe Gln Asn Arg Arg Ala
            115                 120                 125

Arg Thr Lys Leu Lys Gln Thr Glu Met Glu Cys Glu Tyr Leu Lys Arg
            130                 135                 140

Cys Phe Gly Ser Leu Thr Glu Glu Asn Arg Arg Leu Gln Arg Glu Val
145                 150                 155                 160
```

```
Glu Glu Leu Arg Ala Met Arg Val Ala Pro Pro Thr Val Leu Ser Pro
            165                 170                 175

His Thr Arg Gln Pro Leu Pro Ala Ser Ala Leu Thr Met Cys Pro Arg
        180                 185                 190

Cys Glu Arg Ile Thr Ala Ala Thr Gly Pro Pro Ala Val Arg Pro Pro
    195                 200                 205

Pro Ser Ser Ala Ala Ala Ala Ala Pro Ser Pro Phe His Pro Arg Arg
    210                 215                 220

Pro Ser Ala Ala Phe
225

<210> SEQ ID NO 9
<211> LENGTH: 9215
<212> TYPE: DNA
<213> ORGANISM: Artificial
<220> FEATURE:
<223> OTHER INFORMATION: vector

<400> SEQUENCE: 9
```

| | | | | |
|---|---|---|---|---|
| actcaccagt | cacagaaaag | catcttacgg | atggcatgac | agtaagagaa ttatgcagtg | 60 |
| ctgccataac | catgagtgat | aacactgcgg | ccaacttact | tctgacaacg atcggaggac | 120 |
| cgaaggagct | aaccgctttt | ttgcacaaca | tgggggatca | tgtaactcgc cttgatcgtt | 180 |
| gggaaccgga | gctgaatgaa | gccataccaa | acgacgagcg | tgacaccacg atgcctgtag | 240 |
| caatggcaac | aacgttgcgc | aaactattaa | ctggcgaact | acttactcta gcttcccggc | 300 |
| aacaattaat | agactggatg | gaggcggata | aagttgcagg | accacttctg cgctcggccc | 360 |
| ttccggctgg | ctggtttatt | gctgataaat | ctggagccgg | tgagcgtggg tctcgcggta | 420 |
| tcattgcagc | actggggcca | gatggtaagc | cctcccgtat | cgtagttatc tacacgacgg | 480 |
| ggagtcaggc | aactatggat | gaacgaaata | gacagatcgc | tgagataggt gcctcactga | 540 |
| ttaagcattg | gtaactgtca | gaccaagttt | actcatatat | actttagatt gatttaaaac | 600 |
| ttcatttta | atttaaaagg | atctaggtga | agatcctttt | tgataatctc atgaccaaaa | 660 |
| tcccttaacg | tgagttttcg | ttccactgag | cgtcagaccc | cgtagaaaag atcaaaggat | 720 |
| cttcttgaga | tccttttttt | ctgcgcgtaa | tctgctgctt | gcaaacaaaa aaaccaccgc | 780 |
| taccagcggt | ggtttgtttg | ccggatcaag | agctaccaac | tcttttttccg aaggtaactg | 840 |
| gcttcagcag | agcgcagata | ccaaatactg | tccttctagt | gtagccgtag ttaggccacc | 900 |
| acttcaagaa | ctctgtagca | ccgcctacat | acctcgctct | gctaatcctg ttaccagtgg | 960 |
| ctgctgccag | tggcgataag | tcgtgtctta | ccgggttgga | ctcaagacga tagttaccgg | 1020 |
| ataaggcgca | gcggtcgggc | tgaacggggg | gttcgtgcac | acagcccagc ttggagcgaa | 1080 |
| cgacctacac | cgaactgaga | tacctacagc | gtgagctatg | agaaagcgcc acgcttcccg | 1140 |
| aagggagaaa | ggcggacagg | tatccggtaa | gcggcagggt | cggaacagga gagcgcacga | 1200 |
| gggagcttcc | agggggaaac | gcctggtatc | tttatagtcc | tgtcgggttt cgccacctct | 1260 |
| gacttgagcg | tcgatttttg | tgatgctcgt | caggggggcg | gagcctatgg aaaaacgcca | 1320 |
| gcaacgcggc | cttttacgg | ttcctggcct | tttgctggcc | ttttgctcac atgttctttc | 1380 |
| ctgcgttatc | ccctgattct | gtggataacc | gtattaccgc | ctttgagtga gctgataccg | 1440 |
| ctcgccgcag | ccgaacgacc | gagcgcagcg | agtcagtgag | cgaggaagcg gaagagcgcc | 1500 |
| caatacgcaa | accgcctctc | cccgcgcgtt | ggccgattca | ttaatgcagc tggcacgaca | 1560 |
| ggtttcccga | ctggaaagcg | ggcagtgagc | gcaacgcaat | taatgtgagt tagctcactc | 1620 |

```
attaggcacc ccaggcttta cactttatgc ttccggctcg tatgttgtgt ggaattgtga    1680
gcggataaca atttcacaca ggaaacagct atgaccatga ttacgccaag ctcgaaatta    1740
accctcacta aagggaacaa aagctggagc tgagtactgg cgcgcctgcg gccgcctcga    1800
ggtcattcat atgcttgaga agagagtcgg gatagtccaa aataaaacaa aggtaagatt    1860
acctggtcaa aagtgaaaac atcagttaaa aggtggtata agtaaaata tcggtaataa     1920 aagtggccc aaagtgaaat ttactctttt ctactattat aaaaattgag gatgttttg      1980 tcggtacttt gatacgtcat ttttgtatga attggttttt aagtttattc gcttttggaa    2040
atgcatatct gtatttgagt cgggttttaa gttcgtttgc ttttgtaaat acagagggat    2100
ttgtataaga aatatcttta aaaaaccca tatgctaatt tgacataatt tttgagaaaa     2160
atatatattc aggcgaattc tcacaatgaa caataataag attaaaatag ctttcccccg    2220
ttgcagcgca tgggtatttt ttctagtaaa aataaaagat aaacttagac tcaaaacatt    2280
tacaaaaaca acccctaaag ttcctaaagc ccaaagtgct atccacgatc cattagcaag    2340
gcccagccca acccaaccca acccaaccca ccccagtcca gccaactgga caatagtctc    2400
cacccccggc actatcaccg tgagttgtcc gcaccaccgc acgtctcgca gccaaaaaaa    2460 aaaaagaaa gaaaaaaag aaaagaaaa acagcaggtg ggtccgggtc gtggggccg       2520 gaaaagcgag gaggatcgcg agcagcgacg aggcccggcc ctccctccgc ttccaaagaa    2580
acgcccccca tcgccactat atacataccc ccctctcc tcccatcccc caaccctac      2640 caccaccacc accaccacct cctcccccct cgctgccgga cgacgagctc ctcccccctc    2700
cccctccgcc gccgccggta accacccgc ccctctcctc tttctttctc cgttttttt     2760 ttcgtctcgg tctcgatctt tggccttggt agtttgggtg ggcgagagcg gcttcgtcgc    2820
ccagatcggt gcgcgggagg ggcgggatct cgcggctggc gtctccgggc gtgagtcggc    2880
ccggatcctc gcggggaatg gggctctcgg atgtagatct gatccgccgt tgttggggga    2940
gatgatgggg ggtttaaaat ttccgccatg ctaaacaaga tcaggaagag gggaaaaggg    3000
cactatggtt tatattttta tatatttctg ctgcttcgtc aggcttagat gtgctagatc    3060
tttctttctt cttttgtgg gtagaaattg aatccctcag cattgttcat cggtagtttt    3120
tcttttcatg atttgtgaca aatgcagcct cgtgcggagc ttttttgtag gtagaccgcg    3180
ggatatcaca agtttgtaca aaaaagctga acgagaaacg taaatgata taaatatcaa     3240 tatattaaat tagattttgc ataaaaaaca gactacataa tactgtaaaa cacaacatat    3300
ccagtcacta tggcggccgc attaggcacc ccaggcttta cactttatgc ttccggctcg    3360
tataatgtgt ggattttgag ttaggatccg tcgagatttt caggagctaa ggaagctaaa    3420
atggagaaaa aaatcactgg atataccacc gttgatatat cccaatggca tcgtaaagaa    3480
cattttgagg catttcagtc agttgctcaa tgtacctata accagaccgt tcagctggat    3540
attacggcct ttttaaagac cgtaaagaaa aataagcaca gtttatcc ggcctttatt      3600 cacattcttg cccgcctgat gaatgctcat ccggaattcc gtatggcaat gaaagacggt    3660
gagctggtga tatgggatag tgttcaccct tgttacaccg ttttccatga gcaaactgaa    3720
acgttttcat cgctctggag tgaataccac gacgatttcc ggcagtttct acacatatat    3780
tcgcaagatg tggcgtgtta cggtgaaaac ctggcctatt tccctaaagg gtttattgag    3840
aatatgtttt tcgtctcagc caatccctgg gtgagtttca ccagttttga tttaaacgtg    3900
gccaatatgg acaacttctt cgcccccgtt ttcaccatgg gcaaatatta tacccaaggc    3960
```

```
gacaaggtgc tgatgccgct ggcgattcag gttcatcatg ccgtctgtga tggcttccat      4020
gtcggcagaa tgcttaatga attacaacag tactgcgatg agtggcaggg cggggcgtaa      4080
acgcgtggat ccggcttact aaaagccaga taacagtatg cgtatttgcg cgctgatttt      4140
tgcggtataa gaatatatac tgatatgtat acccgaagta tgtcaaaaag aggtgtgcta      4200
tgaagcagcg tattacagtg acagttgaca gcgacagcta tcagttgctc aaggcatata      4260
tgatgtcaat atctccggtc tggtaagcac aaccatgcag aatgaagccc gtcgtctgcg      4320
tgccgaacgc tggaaagcgg aaaatcagga agggatggct gaggtcgccc ggtttattga      4380
aatgaacggc tcttttgctg acgagaacag gggctggtga aatgcagttt aaggtttaca      4440
cctataaaag agagagccgt tatcgtctgt ttgtggatgt acagagtgat attattgaca      4500
cgcccgggcg acggatggtg atccccctgg ccagtgcacg tctgctgtca gataaagtct      4560
cccgtgaact ttacccggtg gtgcatatcg gggatgaaag ctggcgcatg atgaccaccg      4620
atatggccag tgtgccggtc tccgttatcg gggaagaagt ggctgatctc agccaccgcg      4680
aaaatgacat caaaaacgcc attaacctga tgttctgggg aatataaatg tcaggctccc      4740
ttatacacag ccagtctgca ggtcgaccat agtgactgga tatgttgtgt tttacagtat      4800
tatgtagtct gttttttatg caaaatctaa tttaatatat tgatatttat atcattttac      4860
gtttctcgtt cagctttctt gtacaaagtg gtgatgggga tcccccaccc tgcaatgtga      4920
ccctagactt gtccatcttc ggatggccaa cttaattaat gtataaataa aaggatgcac      4980
acatagtgac atgctaatca ctataatgtg ggcatcaaag ttgtgtgtta tgtgtaatta      5040
ctaattatct gaataagaga aagagatcat ccatatttct tatcctaaat gaatgtcacg      5100
tgtctttata attctttgat gaaccagatg cattttatta accaattcca tatacatata      5160
aatattaatc atatataatt aatatcaatt gggttagcaa aacaaatcta gtctaggtgt      5220
gttttgctaa ttattggggg atagtgcaaa agaaatctca cgttctcaat aattcagata      5280
gaaaacttaa taaagtgaga taatttacat agattgcttt tatcctttga tatatgtgaa      5340
accatgcatg atataaggaa aatagataga gaataatttt tttacatcgt tgaatatgta      5400
aacaatttaa ttcaagaagc taggaatata aatattgagg agtttatgat tattattatt      5460
attttgatgt tcaatgaagt ttttttttaat ttcatatgaa gtatacaaaa attcttcata      5520
gattttttgtt tctatgccgt agttatcttt aatatatttg tggttgaaga atttattgc      5580
tagaaacgaa tggattgtca atttttttttt aaagcaaata tatatgaaat tatactgtat      5640
attatttttag tcatgattaa aatgtggcct taattgaatc atctttctca ttcatttttt      5700
caaaagcata tcaggatgat tgatatttat ctattttaaa aattaattta agggttcaaa      5760
ttaaatttaa cttaaaagtg tcctaaccgt agttaaaggt ttactttaaa aaatactat       5820
gaaaaatcta atcttctatg aatcgacctg caggatttaa atccatcgtt ctggggccta      5880
acgggccaag ctttccgatc ctacctgtca cttcatcaaa aggacagtag aaaaggaagg      5940
tggcacctac aaatgccatc attgcgataa aggaaaggct atcattcaag atgcctctgc      6000
cgacagtggt cccaaagatg accccccacc cacgaggagc atcgtggaaa agaagacgt       6060
tccaaccacg tcttcaaagc aagtggattg atgtgatact tccactgacg taagggatga      6120
cgcacaatcc cactatcctt cgcaagaccc ttcctctata taaggaagtt catttcattt      6180
ggagaggaca cgctgaaatc accagtctct ctctacaaga tcgggatct ctagctagac        6240
gatcgtttcg catgattgaa caagatggat tgcacgcagg ttctccggcc gcttgggtgg      6300
agaggctatt cggctatgac tgggcacaac agacaatcgg ctgctctgat gccgccgtgt      6360
```

```
tccggctgtc agcgcagggg cgcccggttc tttttgtcaa gaccgacctg tccggtgccc   6420
tgaatgaact gcaggacgag gcagcgcggc tatcgtggct ggccacgacg ggcgttcctt   6480
gcgcagctgt gctcgacgtt gtcactgaag cgggaaggga ctggctgcta ttgggcgaag   6540
tgccggggca ggatctcctg tcatctcacc ttgctcctgc cgagaaagta tccatcatgg   6600
ctgatgcaat gcggcggctg catacgcttg atccggctac ctgcccattc gaccaccaag   6660
cgaaacatcg catcgagcga gcacgtactc ggatggaagc cggtcttgtc gatcaggatg   6720
atctggacga agagcatcag gggctcgcgc cagccgaact gttcgccagg ctcaaggcgc   6780
gcatgcccga cggcgaggat ctcgtcgtga cccatggcga tgcctgcttg ccgaatatca   6840
tggtggaaaa tggccgcttt tctggattca tcgactgtgg ccggctgggt gtggcggacc   6900
gctatcagga catagcgttg gctacccgtg atattgctga agagcttggc ggcgaatggg   6960
ctgaccgctt cctcgtgctt tacggtatcg ccgctcccga ttcgcagcgc atcgccttct   7020
atcgccttct tgacgagttc ttctgagcgg gactctgggg ttcgaagaat tcccgatcgt   7080
tcaaacattt ggcaataaag tttcttaaga ttgaatcctg ttgccggtct tgcgatgatt   7140
atcatataat ttctgttgaa ttacgttaag catgtaataa ttaacatgta atgcatgacg   7200
ttatttatga gatgggtttt tatgattaga gtcccgcaat tatacattta atacgcgata   7260
gaaaacaaaa tatagcgcgc aaactaggat aaattatcgc gcgcggtgtc atctatgtta   7320
ctagatcggg gatatcgcgt gtctttataa ttctttgatg aaccagatgc attttattaa   7380
ccaattccat atacatataa atattaatca tatataatta atatcaattg ggttagcaaa   7440
acaaatctag tctaggtgtg ttttgctaat tattggggga tagtgcaaaa agaaatctac   7500
gttctcaata attcagatag aaaacttaat aaagtgagat aatttacata gattgctttt   7560
atcctttgat atatgtgaaa ccatgcatga tataaggaaa atagatagag aaataatttt   7620
ttacatcgtt gaatatgtaa acaatttaat tcaagaagct aggaatataa atattgagga   7680
gtttatgatt attattatta ttttgatgtt caatgaagtt ttttttaatt tcatatgaag   7740
tatacaaaaa ttcttcatag atttttgttt ctatgccgta gttatcttta atatatttgt   7800
ggttgaagaa atttattgct agaaacgaat ggattgtcaa ttttttttta aagcaaatat   7860
atatgaaatt atactgtata ttattttagt catgattaaa atgtggcctt aattgaatca   7920
tctttctcat tcattttttc aaaagcatat caggatgatt gatatttatc tattttaaaa   7980
attaatttaa gggttcaaat taaatttaac ttaaaagtgt cctaaccgta gttaaaggtt   8040
tactttaaaa aaatactatg aaaaatctaa tcttctatga atcgaccgct gatcgatcgc   8100
ggccgctggc gcgccagtac tagctagtac ccaattcgcc ctatagtgag tcgtattaca   8160
attcactggc cgtcgtttta caacgtcgtg actgggaaaa ccctggcgtt acccaactta   8220
atcgccttgc agcacatccc cctttcgcca gctggcgtaa tagcgaagag gcccgcaccg   8280 atcgccttc ccaacagttg cgcagcctga atggcgaatg gaaattgtaa gcgttaatat   8340
tttgttaaaa ttcgcgttaa attttttgtta aatcagctca ttttttaacc aataggccga   8400
aatcggcaaa atcccttata aatcaaaaga tagaccgag ataggggttga gtgttgttcc   8460 agtttggaac aagagtccac tattaaagaa cgtggactcc aacgtcaaag ggcgaaaaac   8520
cgtctatcag ggcgatggcc cactacgtga accatcaccc taatcaagtt ttttggggtc   8580
gaggtgccgt aaagcactaa atcggaaccc taaagggagc cccgatttta agcttgacg   8640 gggaaagccg gcgaacgtgg cgagaaagga agggaagaaa gcgaaaggag cgggcgctag   8700
```

```
ggcgctggca agtgtagcgg tcacgctgcg cgtaaccacc acacccgccg cgcttaatgc    8760
gccgctacag ggcgcgtcag gtggcacttt tcggggaaat gtgcgcggaa ccccctatttg   8820 tttatttttc taaatacatt caaatatgta tccgctcatg agacaataac cctgataaat    8880
gcttcaataa tattgaaaaa ggaagagtat gagtattcaa catttccgtg tcgcccttat    8940
tccctttttt gcggcatttt gccttcctgt ttttgctcac ccagaaacgc tggtgaaagt    9000
aaaagatgct gaagatcagt tgggtgcacg agtgggttac atcgaactgg atctcaacag    9060
cggtaagatc cttgagagtt ttcgccccga agaacgtttt ccaatgatga gcacttttaa    9120
agttctgcta tgtggcgcgg tattatcccg tattgacgcc gggcaagagc aactcggtcg    9180
ccgcatacac tattctcaga atgacttggt tgagt                              9215

<210> SEQ ID NO 10
<211> LENGTH: 9747
<212> TYPE: DNA
<213> ORGANISM: Artificial
<220> FEATURE:
<223> OTHER INFORMATION: vector

<400> SEQUENCE: 10
ccgatcctac ctgtcacttc atcaaaagga cagtagaaaa ggaaggtggc acctacaaat      60
gccatcattg cgataaagga aaggctatca ttcaagatgc ctctgccgac agtggtccca    120
aagatggacc cccacccacg aggagcatcg tggaaaaaga acgttccca accacgtctt    180 caaagcaagt ggattgatgt gatacttcca ctgacgtaag ggatgacgca caatcccact    240
atccttcgca agacccttcc tctatataag gaagttcatt tcatttggag aggacacgct    300
gaaatcacca gtctctctct acaagatcgg ggatctctag ctagacgatc gtttcgcatg    360
attgaacaag atggattgca cgcaggttct ccggccgctt gggtggagag gctattcggc    420
tatgactggg cacaacagac aatcggctgc tctgatgccg ccgtgttccg gctgtcagcg    480
caggggcgcc cggttctttt tgtcaagacc gacctgtccg gtgccctgaa tgaactgcag    540
gacgaggcag cgcggctatc gtggctggcc acgacgggcg ttccttgcgc agctgtgctc    600
gacgttgtca ctgaagcggg aagggactgg ctgctattgg gcgaagtgcc ggggcaggat    660
ctcctgtcat ctcaccttgc tcctgccgag aaagtatcca tcatggctga tgcaatgcgg    720
cggctgcata cgcttgatcc ggctacctgc ccattcgacc accaagcgaa acatcgcatc    780
gagcgagcac gtactcggat ggaagccggt cttgtcgatc aggatgatct ggacgaagag    840
catcaggggc tcgcgccagc cgaactgttc gccaggctca aggcgcgcat gcccgacggc    900
gaggatctcg tcgtgaccca tggcgatgcc tgcttgccga atatcatggt ggaaaatggc    960
cgcttttctg gattcatcga ctgtggccgg ctgggtgtgg cggaccgcta tcaggacata   1020
gcgttggcta cccgtgatat tgctgaagag cttggcggcg aatgggctga ccgcttcctc   1080
gtgctttacg gtatcgccgc tcccgattcg cagcgcatcg ccttctatcg ccttcttgac   1140
gagttcttct gagcgggact ctggggttcg aagaattccc gatcgttcaa acatttggca   1200
ataaagtttc ttaagattga atcctgttgc cggtcttgcg atgattatca tataatttct   1260
gttgaattac gttaagcatg taataattaa catgtaatgc atgacgttat ttatgagatg   1320
ggtttttatg attagagtcc cgcaattata catttaatac gcgatagaaa acaaaatata   1380
gcgcgcaaac taggataaat tatcgcgcgc ggtgtcatct atgttactag atcggggata   1440
tcgcgtgtct ttataattct ttgatgaacc agatgcattt tattaaccaa ttccatatac   1500
atataaatat taatcatata taattaatat caattgggtt agcaaaacaa atctagtcta   1560
```

```
ggtgtgtttt gctaattatt gggggatagt gcaaaaagaa atctacgttc tcaataattc    1620
agatagaaaa cttaataaag tgagataatt tacatagatt gcttttatcc tttgatatat    1680
gtgaaaccat gcatgatata aggaaaatag atagagaaat aattttttac atcgttgaat    1740
atgtaaacaa tttaattcaa gaagctagga atataaatat tgaggagttt atgattatta    1800
ttattatttt gatgttcaat gaagtttttt ttaatttcat atgaagtata caaaaattct    1860
tcatagattt ttgtttctat gccgtagtta tctttaatat atttgtggtt gaagaaattt    1920
attgctagaa acgaatggat tgtcaatttt ttttttaaagc aaatatatat gaaattatac    1980
tgtatattat tttagtcatg attaaaatgt ggccttaatt gaatcatctt tctcattcat    2040
tttttcaaaa gcatatcagg atgattgata tttatctatt ttaaaaatta atttaagggt    2100
tcaaattaaa tttaacttaa aagtgtccta accgtagtta aaggtttact ttaaaaaaat    2160
actatgaaaa atcaatcttt ctatgaatcg accgctgatc gatcgcggcc gctggcgcgc    2220
cctcgagagg cctcatctaa gcccccattt ggacgtgaat gtagacacgt cgaaataaag    2280
atttccgaat tagaataatt tgtttattgc tttcgcctat aaatacgacg gatcgtaatt    2340
tgtcgtttta tcaaaatgta ctttcatttt ataataacgc tgcggacatc tacattttttg    2400 aattgaaaaa aaattggtaa ttactctttc tttttctcca tattgaccat catactcatt    2460
gctgatccat gtagatttcc cggacatgaa gccatttaca attgaatata tcctgccgcc    2520
gctgccgctt tgcacccggt ggagcttgca tgttggtttc tacgcagaac tgagccggtt    2580
aggcagataa tttccattga gaactgagcc atgtgcacct tcccccaac acggtgagcg    2640 acggggcaac ggagtgatcc acatgggact tttcctagct tggctgccat ttttgggggtg    2700 aggccgttcg cggccgaggg gcgcagcccc tgggggggatg ggaggcccgc gttagcgggc    2760
cgggagggtt cgagaagggg gggcaccccc cttcggcgtg cgcggtcacg cgcacagggc    2820
gcagccctgg ttaaaaacaa ggtttataaa tattggttta aaagcaggtt aaaagacagg    2880
ttagcggtgg ccgaaaaacg ggcggaaacc cttgcaaatg ctggatttttc tgcctgtgga    2940 cagcccctca aatgtcaata ggtgcgcccc tcatctgtca gcactctgcc cctcaagtgt    3000
caaggatcgc gcccctcatc tgtcagtagt cgcgcccctc aagtgtcaat accgcagggc    3060
acttatcccc aggcttgtcc acatcatctg tgggaaactc gcgtaaaatc aggcgttttc    3120
gccgatttgc gaggctggcc agctccacgt cgccggccga aatcgagcct gcccctcatc    3180
tgtcaacgcc gcgccgggtg agtcggcccc tcaagtgtca acgtccgccc ctcatctgtc    3240
agtgagggca aagttttccg cgaggtatcc acaacgccgg cggccggccg cggtgtctcg    3300
cacacggctt cgacggcgtt tctggcgcgt ttgcagggcc atagacggcc gccagcccag    3360
cggcgagggc aaccagcccg gtgagcgtcg gaaaggtcg atcgaccgat gcccttgaga    3420
gccttcaacc cagtcagctc cttccggtgg gcgcggggca tgactacggt atcagctcac    3480
tcaaaggcgc taatacggtt atccacagaa tcagggggata acgcaggaaa gaacatgtga    3540
gcaaaaggcc agcaaaaggc caggaaccgt aaaaaggccg cgttgctggc gttttttccat    3600 aggctccgcc cccctgacga gcatcacaaa aatcgacgct caagtcagag gtggcgaaac    3660
ccgacaggac tataaagata ccaggcgttt ccccctggaa gctccctcgt gcgctctcct    3720
gttccgaccc tgccgcttac cggatacctg tccgcctttc tcccttcggg aagcgtggcg    3780
ctttctcata gctcacgctg taggtatctc agttcggtgt aggtcgttcg ctccaagctg    3840
ggctgtgtgc acgaaccccc cgttcagccc gaccgctgcg ccttatccgg taactatcgt    3900
```

```
cttgagtcca acccggtaag acacgactta tcgccactgg cagcagccac tggtaacagg    3960
attagcagag cgaggtatgt aggcggtgct acagagttct tgaagtggtg cctaactac    4020
ggctacacta gaagaacagt atttggtatc tgcgctctgc tgaagccagt taccttcgga    4080
aaaagagttg gtagctcttg atccggcaaa caaaccaccg ctggtagcgg tggtttttt    4140
gtttgcaagc agcagattac gcgcagaaaa aaaggatctc aagaagatcc tttgatcttt    4200
tctacggggt ctgacgctca gtggaacgaa aactcacgtt aagggatttt ggtcatgagg    4260
gaagcggtga tcgccgaagt atcgactcaa ctatcagagg tagttggcgt catcgagcgc    4320
catctcgaac cgacgttgct ggccgtacat ttgtacggct ccgcagtgga tggcggcctg    4380
aagccacaca gtgatattga tttgctggtt acggtgaccg taaggcttga tgaaacaacg    4440
cggcgagctt tgatcaacga ccttttggaa acttcggctt ccctggaga gagcgagatt    4500
ctccgcgctg tagaagtcac cattgttgtg cacgacgaca tcattccgtg gcgttatcca    4560
gctaagcgcg aactgcaatt tggagaatgg cagcgcaatg acattcttgc aggtatcttc    4620
gagccagcca cgatcgacat tgatctggct atcttgctga caaaagcaag agaacatagc    4680
gttgccttgg taggtccagc ggcggaggaa ctctttgatc cggttcctga acaggatcta    4740
tttgaggcgc taaatgaaac cttaacgcta tggaactcgc cgcccgactg ggctggcgat    4800
gagcgaaatg tagtgcttac gttgtcccgc atttggtaca gcgcagtaac cggcaaaatc    4860
gcgccgaagg atgtcgctgc cgactgggca atggagcgcc tgccggccca gtatcagccc    4920
gtcatacttg aagctaggca ggcttatctt ggacaagaag atcgcttggc ctcgcgcgca    4980
gatcagttgg aagaatttgt tcactacgtg aaaggcgaga tcaccaaggt agtcggcaaa    5040
taatgtctaa caattcgttc aagccgacgc cgcttcgcgg cgcggcttaa ctcaagcgtt    5100
agatgctgca ggcatcgtgg tgtcacgctc gtcgtttggt atggcttcat tcagctccgg    5160
ttcccaacga tcaaggcgag ttacatgatc ccccatgttg tgcaaaaaag cggttagctc    5220
cttcggtcct ccgatcgagg ttttttcggc gctgcgctac gtccgcgacc gcgttgaggg    5280
atcaagccac agcagcccac tcgaccttct agccgaccca gacgagccaa gggatctttt    5340
tggaatgctg ctccgtcgtc aggctttccg acgtttgggt ggttgaacag aagtcattat    5400
cgcacggaat gccaagcact cccgagggga accctgtggt tggcatgcac atacaaatgg    5460
acgaacggat aaacctttc acgcccttt aaatatccga ttattctaat aaacgctctt    5520
ttctcttagg tttacccgcc aatatatcct gtcaaacact gatagtttaa acatgactct    5580
cttaaggtag ccaaagcccc ggaattcggc gcgcctgcgg ccgcctcgag gtcattcata    5640
tgcttgagaa gagagtcggg atagtccaaa ataaacaaa ggtaagatta cctggtcaaa    5700
agtgaaaaca tcagttaaaa ggtggtataa agtaaaatat cggtaataaa aggtggccca    5760
aagtgaaatt tactcttttc tactattata aaaattgagg atgttttgt cggtactttg    5820
atacgtcatt tttgtatgaa ttggtttta agtttattcg cttttggaaa tgcatatctg    5880
tatttgagtc gggtttaag ttcgtttgct tttgtaaata cagagggatt tgtataagaa    5940
atatctttaa aaaacccat atgctaattt gacataattt ttgagaaaaa tatatattca    6000
ggcgaattct cacaatgaac aataataaga ttaaaatagc tttccccgt tgcagcgcat    6060
gggtatttt tctagtaaaa ataaaagata aacttagact caaacatttt acaaaaacaa    6120
cccctaaagt tcctaaagcc caaagtgcta tccacgatcc atagcaagcc agcccaacc    6180
caacccaacc caacccaccc cagtccagcc aactggacaa tagtctccac acccccccac    6240
tatcaccgtg agttgtccgc acgcaccgca cgtctcgcag ccaaaaaaaa aaaagaaag    6300
```

```
aaaaaaaaga aaaagaaaaa acagcaggtg ggtccgggtc gtgggggccg gaaacgcgag   6360
gaggatcgcg agccagcgac gaggccggcc ctccctccgc ttccaaagaa acgccccca    6420 tcgccactat atacataccc cccctctcc tcccatcccc caacccctac caccaccacc    6480
accaccacct ccacctcctc cccctcgct gccggacgac gagctcctcc ccctcccc     6540 tccgccgccg ccgcgccggt aaccacccg ccctctcct ctttctttct ccgttttttt    6600
tttccgtctc ggtctcgatc tttggccttg gtagtttggg tgggcgagag gcggcttcgt   6660
gcgcgcccag atcggtgcgc gggaggggcg ggatctcgcg gctgggctc tcgccggcgt    6720 ggatccggcc cggatctcgc ggggaatggg gctctcggat gtagatctgc gatccgccgt   6780
tgttggggga gatgatgggg ggtttaaaat ttccgccatg ctaaacaaga tcaggaagag   6840
gggaaaaggg cactatggtt tatattttta tatatttctg ctgcttcgtc aggcttagat   6900
gtgctagatc tttctttctt cttttgtgg gtagaatttg aatccctcag cattgttcat    6960
cggtagtttt tcttttcatg atttgtgaca aatgcagcct cgtgcggagc tttttttgtag  7020 gtagaccgcg ggatatcaca agtttgtaca aaaagctga acgagaaacg taaaatgata    7080
taaatatcaa tatattaaat tagattttgc ataaaaaaca gactacataa tactgtaaaa   7140
cacaacatat ccagtcacta tggcggccgc attaggcacc ccaggcttta cactttatgc   7200
ttccggctcg tataatgtgt ggattttgag ttaggatccg tcgagatttt caggagctaa   7260
ggaagctaaa atggagaaaa aaatcactgg atataccacc gttgatatat cccaatggca   7320
tcgtaaagaa cattttgagg catttcagtc agttgctcaa tgtacctata accagaccgt    7380
tcagctggat attacggcct ttttaaagac cgtaaagaaa aataagcaca agttttatcc    7440
ggcctttatt cacattcttg cccgcctgat gaatgctcat ccggaattcc gtatggcaat    7500
gaaagacggt gagctggtga tatgggatag tgttcaccct tgttacaccg ttttccatga    7560
gcaaactgaa acgttttcat cgctctggag tgaataccac gacgatttcc ggcagtttct   7620
acacatatat tcgcaagatg tggcgtgtta cggtgaaaac ctggcctatt tccctaaagg    7680
gtttattgag aatatgtttt tcgtctcagc caatccctgg gtgagtttca ccagttttga    7740
tttaaacgtg gccaatatgg acaacttctt cgccccccgtt ttcaccatgg gcaaatatta   7800
tacgcaaggc gacaaggtgc tgatgccgct ggcgattcag gttcatcatg ccgtttgtga    7860
tggcttccat gtcggcagaa tgcttaatga attacaacag tactgcgatg agtggcaggg    7920
cggggcgtaa acgcgtggat ccggcttact aaaagccaga taacagtatg cgtatttgcg    7980
cgctgatttt tgcggtataa gaatatatac tgatatgtat acccgaagta tgtcaaaaag    8040
aggtatgcta tgaagcagcg tattacagtg acagttgaca gcgacagcta tcagttgctc    8100
aaggcatata tgatgtcaat atctccggtc tggtaagcac aaccatgcag aatgaagccc    8160
gtcgtctgcg tgccgaacgc tggaaagcgg aaaatcagga agggatggct gaggtcgccc    8220
ggtttattga aatgaacggc tcttttgctg acgagaacag gggctggtga atgcagtttt    8280
aaggtttaca cctataaaag agagagccgt tatcgtctgt ttgtggatgt acagagtgat    8340
attattgaca cgcccgggcg acggatggtg atcccctgg ccagtgcacg tctgctgtca    8400
gataaagtct cccgtgaact ttacccggtg gtgcatatcg gggatgaaag ctggcgcatg    8460
atgaccaccg atatggccag tgtgccggtc tccgttatcg gggaagaagt ggctgatctc    8520
agccaccgcg aaaatgacat caaaaacgcc attaacctga tgttctgggg aatataaatg    8580
tcaggctccc ttatacacag ccagtctgca ggtcgaccat agtgactgga tatgttgtgt    8640
```

-continued

```
tttacagtat tatgtagtct gttttttatg caaaatctaa tttaatatat tgatatttat    8700
atcattttac gtttctcgtt cagctttctt gtacaaagtg gtgatgggga tcccccaccc    8760
tgcaatgtga ccctagactt gtccatcttc tggattggcc aacttaatta atgtatgaaa    8820
taaaaggatg cacacatagt gacatgctaa tcactataat gtgggcatca aagttgtgtg    8880
ttatgtgtaa ttactaatta tctgaataag agaaagagat catccatatt tcttatccta    8940
aatgaatgtc acgtgtcttt ataattcttt gatgaaccag atgcattta ttaaccaatt     9000
ccatatacat ataaatatta atcatatata attaatatca attgggttag caaaacaaat    9060
ctagtctagg tgtgttttgc taattattgg gggatagtgc aaaaagaaat ctacgttctc    9120
aataattcag atagaaaact taataaagtg agataattta catagattgc ttttatcctt    9180
tgatatatgt gaaaccatgc atgatataag gaaatatagat agagaaataa ttttttacat   9240
cgttgaatat gtaaacaatt taattcaaga agctaggaat ataaatattg aggagtttat    9300
gattattatt attattttga tgttcaatga agttttttt aatttcatat gaagtataca     9360
aaaattcttc atagattttt gtttctatgc cgtagttatc tttaatatat ttgtggttga    9420
agaaatttat tgctagaaac gaatggattg tcaatttttt tttaaagcaa atatatatga    9480
aattatactg tatattattt tagtcatgat taaaatgtgg ccttaattga atcatctttc    9540
tcattcattt tttcaaaagc atatcaggat gattgatatt tatctatttt aaaaattaat   9600
ttaagggttc aaattaaatt taacttaaaa gtgtcctaac cgtagttaaa ggtttacttt    9660
aaaaaaatac tatgaaaaat ctaatcttct atgaatcgac ctgcaggatt taaatccatc    9720
gttctggggc ctaacgggcc aagcttt                                        9747
```

<210> SEQ ID NO 11
<211> LENGTH: 1023
<212> TYPE: PRT
<213> ORGANISM: Artificial
<220> FEATURE:
<223> OTHER INFORMATION: promoter

<400> SEQUENCE: 11

```
Ala Gly Cys Thr Thr Ala Thr Cys Gly Gly Cys Cys Gly Ala Gly Gly
1               5                   10                  15

Thr Gly Ala Gly Ala Ala Gly Gly Thr Thr Cys Thr Ala Ala Ala
            20                  25                  30

Gly Ala Cys Ala Thr Gly Gly Ala Gly Gly Thr Gly Ala Ala Ala Gly
        35                  40                  45

Gly Cys Cys Thr Gly Ala Cys Gly Thr Ala Gly Ala Thr Ala Gly Ala
    50                  55                  60

Gly Ala Ala Gly Ala Thr Gly Cys Thr Cys Thr Ala Gly Cys Thr
65                  70                  75                  80

Thr Thr Cys Ala Thr Thr Gly Thr Cys Thr Thr Cys Thr Thr Thr
                85                  90                  95

Thr Gly Thr Ala Gly Thr Cys Ala Thr Cys Gly Ala Thr Thr Thr
            100                 105                 110

Ala Cys Cys Thr Cys Thr Cys Thr Cys Gly Thr Thr Ala Thr Ala
        115                 120                 125

Cys Ala Ala Cys Thr Gly Gly Thr Thr Thr Thr Thr Ala Ala Ala
    130                 135                 140

Cys Ala Cys Thr Cys Cys Thr Thr Ala Ala Cys Thr Thr Thr Cys
145                 150                 155                 160

Ala Ala Ala Thr Thr Gly Thr Cys Thr Cys Thr Thr Thr Cys Thr Thr
```

-continued

```
                165                 170                 175
Thr Ala Cys Cys Cys Thr Ala Gly Ala Cys Thr Ala Gly Ala Thr Ala
            180                 185                 190
Ala Thr Thr Thr Thr Ala Ala Thr Gly Gly Thr Gly Ala Thr Thr Thr
        195                 200                 205

Thr Gly Cys Thr Ala Ala Thr Gly Thr Gly Gly Cys Gly Cys Cys Ala
    210                 215                 220

Thr Gly Thr Thr Ala Gly Ala Thr Ala Gly Ala Gly Gly Thr Ala Ala
225                 230                 235                 240
Ala Ala Thr Gly Ala Ala Cys Thr Ala Gly Thr Thr Ala Ala Ala Ala
                245                 250                 255

Gly Cys Thr Cys Ala Gly Ala Gly Thr Gly Ala Thr Ala Ala Ala Thr
            260                 265                 270
Cys Ala Gly Gly Cys Thr Cys Thr Cys Ala Ala Ala Ala Ala Thr Thr
        275                 280                 285

Cys Ala Thr Ala Ala Ala Cys Thr Gly Thr Thr Thr Thr Thr Thr Ala
    290                 295                 300

Ala Ala Thr Ala Thr Cys Cys Ala Ala Ala Thr Ala Thr Thr Thr Thr
305                 310                 315                 320
Thr Ala Cys Ala Thr Gly Gly Ala Ala Ala Ala Thr Ala Ala Thr Ala
                325                 330                 335

Ala Ala Ala Thr Thr Thr Ala Gly Thr Thr Thr Ala Gly Thr Ala Thr
            340                 345                 350

Thr Ala Ala Ala Ala Ala Ala Thr Thr Cys Ala Gly Thr Thr Gly Ala
        355                 360                 365

Ala Thr Ala Thr Ala Gly Thr Thr Thr Thr Gly Thr Cys Thr Thr Cys
    370                 375                 380

Ala Ala Ala Ala Ala Thr Thr Ala Thr Gly Ala Ala Ala Cys Thr Gly
385                 390                 395                 400
Ala Thr Cys Thr Thr Ala Ala Thr Thr Ala Thr Thr Thr Thr Thr Cys
                405                 410                 415

Cys Thr Thr Ala Ala Ala Ala Cys Cys Gly Thr Gly Cys Thr Cys Thr
            420                 425                 430
Ala Thr Cys Thr Thr Thr Gly Ala Thr Gly Thr Cys Thr Ala Gly Thr
        435                 440                 445

Thr Thr Gly Ala Gly Ala Cys Gly Ala Thr Thr Ala Thr Ala Thr Ala
    450                 455                 460

Ala Thr Thr Thr Thr Thr Thr Thr Thr Gly Thr Gly Cys Thr Thr Ala
465                 470                 475                 480
Ala Cys Thr Ala Cys Gly Ala Cys Gly Ala Gly Cys Thr Gly Ala Ala
                485                 490                 495

Gly Thr Ala Cys Gly Thr Ala Gly Ala Ala Ala Thr Ala Cys Thr Ala
            500                 505                 510
Gly Thr Gly Gly Ala Gly Thr Cys Gly Thr Gly Cys Cys Gly Cys Gly
        515                 520                 525

Thr Gly Thr Gly Cys Cys Thr Gly Thr Ala Gly Cys Cys Ala Cys Thr
    530                 535                 540

Cys Gly Thr Ala Cys Gly Cys Thr Ala Cys Ala Gly Cys Cys Cys Ala
545                 550                 555                 560

Ala Gly Cys Gly Cys Thr Ala Gly Ala Gly Cys Cys Cys Ala Ala Gly
                565                 570                 575

Ala Gly Gly Cys Cys Gly Gly Ala Gly Gly Thr Gly Gly Ala Ala Gly
            580                 585                 590
```

```
Gly Cys Gly Thr Cys Gly Cys Gly Gly Cys Ala Cys Thr Ala Thr Ala
            595                 600                 605

Gly Cys Cys Ala Cys Thr Cys Gly Cys Cys Gly Cys Ala Ala Gly Ala
            610                 615                 620

Gly Cys Cys Cys Ala Ala Gly Ala Gly Ala Cys Cys Gly Gly Ala Gly
625                 630                 635                 640

Cys Thr Gly Gly Ala Ala Gly Gly Ala Thr Gly Ala Gly Gly Gly Thr
                645                 650                 655

Cys Thr Gly Gly Gly Thr Gly Thr Thr Cys Ala Cys Gly Ala Ala Thr
                660                 665                 670

Thr Gly Cys Cys Thr Gly Gly Ala Gly Gly Cys Ala Gly Gly Ala Gly
            675                 680                 685

Gly Cys Thr Cys Gly Thr Cys Gly Thr Cys Cys Gly Gly Ala Gly Cys
            690                 695                 700

Cys Ala Cys Ala Gly Gly Cys Gly Thr Gly Gly Ala Gly Ala Cys Gly
705                 710                 715                 720

Thr Cys Cys Gly Gly Gly Ala Thr Ala Ala Gly Gly Thr Gly Ala Gly
                725                 730                 735

Cys Ala Gly Cys Cys Gly Cys Thr Gly Cys Gly Ala Thr Ala Gly Gly
            740                 745                 750

Gly Gly Cys Gly Cys Gly Thr Gly Thr Gly Ala Ala Cys Cys Cys Cys
            755                 760                 765

Gly Thr Cys Gly Cys Gly Cys Cys Cys Ala Cys Gly Gly Ala Thr
            770                 775                 780

Gly Gly Thr Ala Thr Ala Ala Gly Ala Ala Thr Ala Ala Ala Gly Gly
785                 790                 795                 800

Cys Ala Thr Thr Cys Cys Gly Cys Gly Thr Gly Cys Ala Gly Gly Ala
                805                 810                 815

Thr Thr Cys Ala Cys Cys Cys Gly Thr Thr Cys Gly Cys Cys Thr Cys
                820                 825                 830

Thr Cys Ala Cys Cys Thr Thr Thr Cys Gly Cys Thr Gly Thr Ala
            835                 840                 845

Cys Thr Cys Ala Cys Thr Cys Gly Cys Cys Ala Cys Ala Cys Ala Cys
            850                 855                 860

Ala Cys Cys Cys Cys Thr Cys Thr Cys Cys Ala Gly Cys Thr Cys
865                 870                 875                 880

Cys Gly Thr Thr Gly Gly Ala Gly Cys Thr Cys Cys Gly Gly Ala Cys
                885                 890                 895

Ala Gly Cys Ala Gly Cys Ala Gly Cys Gly Cys Gly Gly Gly Gly
            900                 905                 910

Cys Gly Gly Thr Cys Ala Cys Gly Cys Thr Ala Gly Thr Ala Ala Gly Cys
            915                 920                 925

Ala Gly Cys Thr Cys Thr Cys Gly Gly Cys Thr Cys Cys Cys Thr Cys
930                 935                 940

Thr Cys Cys Cys Cys Thr Gly Cys Thr Cys Ala Thr Ala Thr
945                 950                 955                 960

Gly Ala Thr Cys Gly Thr Cys Gly Ala Ala Cys Cys Ala Thr Cys
                965                 970                 975

Gly Ala Gly Cys Thr Ala Cys Ala Ala Cys Gly Gly Thr Thr Cys Thr
            980                 985                 990

Cys Ala Cys Cys Gly Cys Gly Gly Cys Gly Cys Gly Ala Thr Thr
            995                1000                1005
```

```
Thr Cys  Cys Ala Gly Cys Ala  Gly Cys Cys Cys Gly  Gly Gly Gly
    1010             1015                  1020
```

<210> SEQ ID NO 12
<211> LENGTH: 804
<212> TYPE: DNA
<213> ORGANISM: Artificial
<220> FEATURE:
<223> OTHER INFORMATION: element

<400> SEQUENCE: 12

| | | | | | |
|---|---|---|---|---|---|
| accgtcttcg | gtacgcgctc | actccgccct | ctgcctttgt | tactgccacg | tttctctgaa | 60 |
| tgctctcttg | tgtggtgatt | gctgagagtg | gtttagctgg | atctagaatt | acactctgaa | 120 |
| atcgtgttct | gcctgtgctg | attacttgcc | gtcctttgta | gcagcaaaat | atagggacat | 180 |
| ggtagtacga | aacgaagata | gaacctacac | agcaatacga | gaaatgtgta | atttggtgct | 240 |
| tagcggtatt | tatttaagca | catgttggtg | ttatagggca | cttggattca | gaagtttgct | 300 |
| gttaatttag | gcacaggctt | catactacat | gggtcaatag | tatagggatt | catattatag | 360 |
| gcgatactat | aataatttgt | tcgtctgcag | agcttattat | ttgccaaaat | tagatattcc | 420 |
| tattctgttt | ttgtttgtgt | gctgttaaat | tgttaacgcc | tgaaggaata | aatataaatg | 480 |
| acgaaatttt | gatgtttatc | tctgctcctt | tattgtgacc | ataagtcaag | atcagatgca | 540 |
| cttgttttaa | atattgttgt | ctgaagaaat | aagtactgac | agtatttga | tgcattgatc | 600 |
| tgcttgtttg | ttgtaacaaa | atttaaaaat | aaagagtttc | cttttgttg | ctctccttac | 660 |
| ctcctgatgg | tatctagtat | ctaccaactg | acactatatt | gcttctcttt | acatacgtat | 720 |
| cttgctcgat | gccttctccc | tagtgttgac | cagtgttact | cacatagtct | ttgctcattt | 780 |
| cattgtaatg | cagataccaa | gcgg | | | | 804 |

<210> SEQ ID NO 13
<211> LENGTH: 9754
<212> TYPE: DNA
<213> ORGANISM: Artificial
<220> FEATURE:
<223> OTHER INFORMATION: vector

<400> SEQUENCE: 13

| | | | | | |
|---|---|---|---|---|---|
| gatggggatc | agattgtcgt | ttcccgcctt | cagtttaaac | tatcagtgtt | tgacaggata | 60 |
| tattggcggg | taaacctaag | agaaaagagc | gtttattaga | ataatcggat | atttaaaagg | 120 |
| gcgtgaaaag | gtttatccgt | tcgtccattt | gtatgtgcat | gccaaccaca | gggttccct | 180 |
| cgggagtgct | tggcattccg | tgcgataatg | acttctgttc | aaccacccaa | acgtcggaaa | 240 |
| gcctgacgac | ggagcagcat | tccaaaaaga | tcccttggct | cgtctgggtc | ggctagaagg | 300 |
| tcgagtgggc | tgctgtggct | tgatccctca | acgcggtcgc | ggacgtagcg | cagcgccgaa | 360 |
| aaatcctcga | tcggaggacc | gaaggagcta | accgcttttt | tgcacaacat | ggggatcat | 420 |
| gtaactcgcc | ttgatcgttg | ggaaccggag | ctgaatgaag | ccataccaaa | cgacgagcgt | 480 |
| gacaccacga | tgcctgcagc | atctaacgct | tgagttaagc | cgcgccgcga | agcggcgtcg | 540 |
| gcttgaacga | attgttagac | attatttgcc | gactaccttg | gtgatctcgc | ctttcacgta | 600 |
| gtgaacaaat | tcttccaact | gatctgcgcg | cgaggccaag | cgatcttctt | gtccaagata | 660 |
| agcctgccta | gcttcaagta | tgacgggctg | atactgggcc | ggcaggcgct | ccattgccca | 720 |
| gtcggcagcg | acatccttcg | gcgcgatttt | gccggttact | gcgctgtacc | aaatgcggga | 780 |
| caacgtaagc | actacatttc | gctcatcgcc | agcccagtcg | ggcggcgagt | tccatagcgt | 840 |

```
taaggtttca tttagcgcct caaatagatc ctgttcagga accggatcaa agagttcctc    900
cgccgctgga cctaccaagg caacgctatg ttctcttgct tttgtcagca agatagccag    960
atcaatgtcg atcgtggctg gctcgaagat acctgcaaga atgtcattgc gctgccattc   1020
tccaaattgc agttcgcgct tagctggata acgccacgga atgatgtcgt cgtgcacaac   1080
aatggtgact tctacagcgc ggagaatctc gctctctcca ggggaagccg aagtttccaa   1140
aaggtcgttg atcaaagctc gccgcgttgt ttcatcaagc cttacggtca ccgtaaccag   1200
caaatcaata tcactgtgtg gcttcaggcc gccatccact gcggagccgt acaaatgtac   1260
ggccagcaac gtcggttcga gatggcgctc gatgacgcca actacctctg atagttgagt   1320
cgatacttcg gcgatcaccg cttccctcat gatgtttaac tcctgaatta agccgcgccg   1380
cgaagcggtg tcggcttgaa tgaattgtta ggcgtcatcc tgtgctcccg acctgcagca   1440
atggcaacaa cgttgcgcaa actattaact ggcgaactac ttactctagc ttcccggcaa   1500
caattaatag actggatgga ggcggataaa gttgcaggac cacttctgcg ctcggccctt   1560
ccggctggct ggtttattgc tgataaatct ggagccggtg agcgtgggtc tcgcggtatc   1620
attgcagcac tggggccaga tggtaagccc tcccgtatcg tagttatcta cacgacgggg   1680
agtcaggcaa ctatgatga acgaaataga cagatcgctg agataggtgc ctcactgatt   1740
aagcattggt aactgtcaga ccaagtttac tcatatatac tttagattga tttaaaactt   1800
cattttaat ttaaaaggat ctaggtgaag atccttttg ataatctcat gaccaaaatc   1860
ccttaacgtg agttttcgtt ccactgagcg tcagacccg tagaaaagat caaaggatct   1920
tcttgagatc ctttttttct gcgcgtaatc tgctgcttgc aaacaaaaaa accaccgcta   1980
ccagcggtgg tttgtttgcc ggatcaagag ctaccaactc ttttccgaa ggtaactggc   2040
ttcagcagag cgcagatacc aaatactgtc cttctagtgt agccgtagtt aggccaccac   2100
ttcaagaact ctgtagcacc gcctacatac ctcgctctgc taatcctgtt accagtggct   2160
gctgccagtg gcgataagtc gtgtcttacc gggttggact caagacgata gttaccggat   2220
aaggcgcagc ggtcgggctg aacggggggt tcgtgcacac agcccagctt ggagcgaacg   2280
acctacaccg aactgagata cctacagcgt gagctatgag aaagcgccac gcttcccgaa   2340
gggagaaagg cggacaggta tccggtaagc ggcagggtcg aacaggaga gcgcacgagg   2400
gagcttccag ggggaaacgc ctggtatctt tatagtcctg tcgggtttcg ccacctctga   2460
cttgagcgtc gatttttgtg atgctcgtca gggggcgga gcctatggaa aaacgccagc   2520
aacgcggcct ttttacggtt cctggccttt tgctggcctt tgctcacat gttcttttcct   2580
gcgttatccc ctgattctgt ggataaccgt attaccgcct ttgagtgagc tgataccgct   2640
cgccgcagcc gaacgaccga gcgcagcgag tcagtgagcg aggaagcgga agagcgcctg   2700
atgcggtatt ttctccttac gcatctgtgc ggtatttcac accgcatatg gtgcactctc   2760
agtacaatct gctctgatgc cgcatagtta agccagtata cactccgcta tcgctacgtg   2820
actgggtcat ggctgcgccc cgacacccgc caacacccgc tgacgcgccc tgacgggctt   2880
gtctgctccc ggcatccgct tacagacaag ctgtgaccgt ctccgggagc tgcatgtgtc   2940
agaggttttc accgtcatca ccgaaacgcg cgaggcagct gcggtaaagc tcatcagcgt   3000
ggtcgtgaag cgattcacag atgtctgcct gttcatccgc gtccagctcg ttgagtttct   3060
ccagaagcgt taatgtctgg cttctgataa agcgggccat gttaagggcg gttttttcct   3120
gtttggtcac tgatgcctcc gtgtaagggg gatttctgtt catgggggta atgataccga   3180
tgaaacgaga gaggatgctc acgatacggg ttactgatga tgaacatgcc cggttactgg   3240
```

```
aacgttgtga gggtaaacaa ctggcggtat ggatgcggcg ggaccagaga aaaatcactc   3300
agggtcaatg ccagcgcttc gttaatacag atgtaggtgt tccacagggt agccagcagc   3360
atcctgcgat gcagatccgg aacataatgg tgcagggcgc tgacttccgc gtttccagac   3420
tttacgaaac acggaaaccg aagaccattc atgttgttgc tcaggtcgca gacgttttgc   3480
agcagcagtc gcttcacgtt cgctcgcgta tcggtgattc attctgctaa ccagtaaggc   3540
aaccccgcca gcctagccgg gtcctcaacg acaggagcac gatcatgcgc acccgtggcc   3600
aggacccaac gctgcccgag atgcgccgcg tgcggctgct ggagatggcg gacgcgatgg   3660
atatgttctg ccaaggggttg gtttgcgcat tcacagttct ccgcaagaat tgattggctc   3720
caattcttgg agtggtgaat ccgttagcga ggtgccgccg gcttccattc aggtcgaggt   3780
ggcccggctc catgcaccgc gacgcaacgc ggggaggcag acaaggtata gggcggcgcc   3840
tacaatccat gccaacccgt tccatgtgct cgccgaggcg gcataaatcg ccgtgacgat   3900
cagcggtcca atgatcgaag ttaggctggt aagagccgcg agcgatcctt gaagctgtcc   3960
ctgatggtcg tcatctacct gcctggacag catggcctgc aacgcgggca tcccgatgcc   4020
gccggaagcg agaagaatca taatgggaa ggccatccag cctcgcgtcg cgaacgccag   4080
caagacgtag cccagcgcgt cggccgccat gccggcgata atggcctgct tctcgccgaa   4140
acgtttggtg gcgggaccag tgacgaaggc ttgagcgagg gcgtgcaaga ttccgaatac   4200
cgcaagcgac aggccgatca tcgtcgcgct ccagcgaaag cggtcctcgc cgaaaatgac   4260
ccagagcgct gccggcacct gtcctacgag ttgcatgata aagaagacag tcataagtgc   4320
ggcgacgata gtcatgcccc gcgcccaccg gaaggagctg actgggttga aggctctcaa   4380
gggcatcggt cgatcgaccc tttccgacgc tcaccgggct ggttgccctc gccgctgggc   4440
tggcggccgt ctatggccct gcaaacgcgc cagaaacgcc gtcgaagccg tgtgcgagac   4500
accgcggccg gccgccggcg ttgtggatac ctcgcgaaaa acttggccct cactgacaga   4560
tgaggggcgg acgttgacac ttgaggggcc gactcacccg gcgcggcgtt gacagatgag   4620
gggcaggctc gatttcggcc ggcgacgtgg agctggccag cctcgcaaat cggcgaaaac   4680
gcctgatttt acgcgagttt cccacagatg atgtggacaa gcctggggat aagtgccctg   4740
cggtattgac acttgagggg cgcgactact gacagatgag gggcgcgatc cttgacactt   4800
gaggggcaga gtgctgacag atgaggggcg caccctattga catttgaggg gctgtccaca   4860
ggcagaaaat ccagcatttg caagggtttc cgcccgtttt tcggccaccg ctaacctgtc   4920 tttaacctg ctttttaaacc aatatttata aaccttgttt ttaaccaggg ctgcgccctg   4980
tgcgcgtgac cgcgcacgcc gaaggggggt gccccccctt ctcgaaccct cccggcccgc   5040
taacgcgggc ctcccatccc cccaggggct gcgcccctcg gccgcgaacg gcctcacccc   5100
aaaaatggca gccaagctag gaaaagtccc atgtggatca ctccgttgcc ccgtcgctca   5160
ccgtgttggg gggaaggtgc acatggctca gttctcaatg gaaattatct gcctaaccgg   5220
ctcagttctg cgtagaaacc aacatgcaag ctccaccggg tgcaaagcgg cagcggcggc   5280
aggatatatt caattgtaaa tggcttcatg tccgggaaat ctacatggat cagcaatgag   5340
tatgatggtc aatatggaga aaagaaaga gtaattacca attttttttc aattcaaaaa   5400
tgtagatgtc cgcagcgtta ttataaaatg aaagtacatt ttgataaaac gacaaattac   5460
gatccgtcgt atttataggc gaaagcaata aacaaattat tctaattcgg aaatctttat   5520
ttcgacgtgt ctacattcac gtccaaatgg gggcttagat gagaaacttc acgatcgatg   5580
```

```
cggccaccac tcgagaagct tactagtcaa caattggcca atctttgttc taaattgcta    5640
ataaacgacc atttccgtca attctccttg gttgcaacag tctacccgtc aaatgtttac    5700
taatttataa gtgtgaagtt tgaattatga aagacgaaat cgtattaaaa attcacaaga    5760
ataaacaact ccatagattt tcaaaaaaac agtcacgaga aaaaaccac agtccgtttg     5820 tctgctcttc tagtttttat tattttcta ttaatagttt tttgttattt cgagaataaa    5880
atttgaacga tgtccgaacc acaaaagccg agccgataaa tcctaagccg agcctaactt    5940
tagccgtaac catcagtcac ggctcccggg ctaattcatt tgaaccgaat cataatcaac    6000
ggtttagatc aaactcaaaa caatctaacg gcaacataga cgcgtcggtg agctaaaaag    6060
agtgtgaaag ccaggtcacc atagcattgt ctctcccaga ttttttattt gggaaataat    6120
agaagaaata gaaaaaaata aaagagtgag aaaaatcgta gagctatata ttcgcacatg    6180
tactcgtttc gctttcctta gtgttagctg ctgccgctgt tgtttctcct ccatttctct    6240
atctttctct ctcgctgctt ctcgaatctt ctgtatcatc ttcttcttct tcaaggtgag    6300
tctctagatc cgttcgcttg attttgctgc tcgttagtcg ttattgttga ttctctatgc    6360
cgatttcgct agatctgttt agcatgcgtt gtggttttat gagaaaatct ttgttttggg    6420
ggttgcttgt tatgtgattc gatccgtgct tgttggatcg atctgagcta attcttaagg    6480
tttatgtgtt agatctatgg agtttgagga ttcttctcgc ttctgtcgat ctctcgctgt    6540 tattttgtt ttttcagtg aagtgaagtt gtttagttcg aaatgacttc gtgtatgctc     6600
gattgatctg gttttaatct tcgatctgtt aggtgttgat gtttacaagt gaattctagt    6660
gttttctcgt tgagatctgt gaagtttgaa cctagttttc tcaataatca acatatgaag    6720
cgatgtttga gtttcaataa acgctgctaa tcttcgaaac taagttgtga tctgattcgt    6780
gtttacttca tgagcttatc caattcattt cggtttcatt ttactttttt tttagtgaac    6840
catggcgcaa gttagcagaa tctgcaatgg tgtgcagaac ccatctctta tctccaatct    6900
ctcgaaatcc agtcaacgca aatctccctt atcggtttct ctgaagacgc agcagcatcc    6960
acgagcttat ccgatttcgt cgtcgtgggg attgaagaag agtgggatga cgttaattgg    7020
ctctgagctt cgtcctctta aggtcatgtc ttctgttccc acggcgtgca tgcttcatgg    7080
agcttcatct aggccagcta ctgccaggaa gtctagcggg ctcagtggca ccgtgcgcat    7140
ccctggcgat aaaagtattt cacacaggag cttcatgttc ggaggacttg ctagtggaga    7200
gacgagaatc actggtttgc ttgagggcga agatgttatc aacaccggta aggcgatgca    7260
agcaatgggt gccagaatcc gaaaagaggg cgatacgtgg atcatcgacg gtgttggtaa    7320
cggaggattg ctcgctcccg aagcgccact tgactttggg aacgcagcta cggggtgccg    7380
tcttactatg ggactggtag gcgtgtatga cttttgactct accttcatcg gtgacgcgag    7440
cctcactaag agaccaatgg gacgagtgct gaatcccctg agggagatgg gtgtccaggt    7500
gaaatctgag gatggtgatc gtcttccggt tactctgcga ggccccaaga cccccacgcc    7560
aatcacgtac agggttccga tggcgtcagc acaggtcaag tcagcggtac tcctggcggg    7620
cctcaacaca cctggaatca caaccgtgat tgaacccatc atgactagag accacacgga    7680
gaagatgttg cagggtttcg gcgctaatct aacggtcgaa accgacgccg acggcgtgag    7740
gacaatccgc ttggagggca gaggtaaact gactggccaa gtcatcgatg tgcctggaga    7800
tccctcgtcc acagcgtttc ccctcgtagc tgcgttgctc gtccctggat ctgatgtgac    7860
gatcctgaat gtcctcatga atccaactag aaccggcctc atcctcacat tgcaggagat    7920
gggtgctgac atcgaggtta tcaatcctag gttggcaggt ggagaggatg tggccgatct    7980
```

-continued

```
gcgcgtgcgt tctagtacac tcaaaggcgt gaccgtccct gaggatcgcg ctccatccat    8040
gatcgacgag taccccattc tcgccgttgc tgctgcgttt gccgagggcg caactgtaat    8100
gaacggcctt gaggagttga gggttaagga gagtgacagg ctgtccgcgg tggcgaatgg    8160
cctgaagcta acggcgtgg actgcgacga aggtgaaacg tcccttgtag tccgtggtcg     8220
cccagacggg aaggggttgg ggaatgcttc gggagctgct gtggcgacgc accttgatca    8280
tagaatcgcc atgtcatttc tggtgatggg acttgtctcc gagaatccgg tgaccgttga    8340
cgatgctacc atgatcgcca cctccttcc tgagttcatg gacctcatgg caggcttggg     8400
ggccaagatc gagctgtctg atactaaggc cgcttgaatt cccgatcgtt caaacatttg    8460
gcaataaagt ttcttaagat tgaatcctgt tgccggtctt gcgatgatta tcatataatt    8520
tctgttgaat tacgttaagc atgtaataat taacatgtaa tgcatgacgt tatttatgag    8580
atgggttttt atgattagag tcccgcaatt atacatttaa tacgcgatag aaaacaaaat    8640
atagcgcgca aactaggata aattatcgcg cgcggtgtca tctatgttac tagatcgggg    8700
atcccacgtg cggaccgcct gcaggccgcg ttatcaagct aactgcaggt ccgatgtgag    8760
acttttcaac aaagggtaat atccggaaac ctcctcggat tccattgccc agctatctgt    8820
cactttattg tgaagatagt ggaaaaggaa ggtggctcct acaaatgcca tcattgcgat    8880
aaaggaaagg ccatcgttga agatgcctct gccgacagtg gtcccaaaga tggaccccca    8940
cccacgagga gcatcgtgga aaaagaagac gttccaacca cgtcttcaaa gcaagtggat    9000
tgatgtgatg gtccgattga gacttttcaa caaagggtaa tatccggaaa cctcctcgga    9060
ttccattgcc cagctatctg tcactttatt gtgaagatag tggaaaagga aggtggctcc    9120
tacaaatgcc atcattgcga taaaggaaag gccatcgttg aagatgcctc tgccgacagt    9180
ggtcccaaag atggaccccc acccacgagg agcatcgtgg aaaaagaaga cgttccaacc    9240
acgtcttcaa gcaagtgga ttgatgtgat atctccactg acgtaaggga tgacgcacaa     9300
tcccactatc cttcgcaaga cccttcctct atataaggaa gttcatttca tttggagagg    9360
accaggtggt accggcgcgc caggcctggt agtctgatta ttaagcgat cgcgggccct     9420 gatcacctgt cgtacagtat ttctacattt gatgtgtgat ttgtgaagaa catcaaacaa    9480
aacaagcact ggctttaata tgatgataag tattatggta attaattaat tggcaaaaac    9540
aacaatgaag ctaaaatttt atttattgag ccttgcggtt aatttcttgt gatgatcttt    9600
ttttttattt tctaattata tatagtttcc tttgctttga aatgctaaag gtttgagaga    9660
gttatgctct tttttttcttc ctctttcttt tttaacttta tcatacaaat tttgaataaa    9720
aatgtgagta cattgagctc atttaaataa gctt                                9754
```

<210> SEQ ID NO 14  
<211> LENGTH: 1696  
<212> TYPE: DNA  
<213> ORGANISM: Artificial  
<220> FEATURE:  
<223> OTHER INFORMATION: element

<400> SEQUENCE: 14

```
caaatttatt atgtgttttt tttccgtggt cgagattgtg tattattctt tagttattac     60
aagactttta gctaaaattt gaaagaattt actttaagaa aatcttaaca tctgagataa    120
tttcagcaat agattatatt tttcattact ctagcagtat ttttgcagat caatcgcaac    180
atatatggtt gttagaaaaa atgcactata tatatatata ttatttttc aattaaaagt     240
```

```
gcatgatata taatatatat atatatatat atgtgtgtgt gtatatggtc aaagaaattc      300
ttatacaaat atacacgaac acatatattt gacaaaatca aagtattaca ctaaacaatg      360
agttggtgca tggccaaaac aaatatgtag attaaaaatt ccagcctcca aaaaaaaatc      420
caagtgttgt aaagcattat atatatatag tagatcccaa attttttgtac aattccacac     480 tgatcgaatt tttaaagttg aatatctgac gtaggatttt tttaatgtct tacctgacca      540
tttactaata acattcatac gttttcattt gaaatatcct ctataattat attgaatttg      600
gcacataata agaaacctaa ttggtgattt attttactag taaatttctg gtgatgggct      660
ttctactaga aagctctcgg aaaatcttgg accaaatcca tattccatga cttcgattgt      720
taaccctatt agttttcaca acatactat caatatcatt gcaacggaaa aggtacaagt       780
aaaacattca atccgatagg gaagtgatgt aggaggttgg gaagacaggc ccagaaagag      840
atttatctga cttgttttgt gtatagtttt caatgttcat aaaggaagat ggagacttga      900
gaagtttttt ttggactttg tttagctttg ttgggcgttt ttttttttga tcaataactt      960
tgttgggctt atgatttgta atattttcgt ggactcttta gttatttag acgtgctaac      1020 tttgttgggc ttatgacttg ttgtaacata ttgtaacaga tgacttgatg tgcgactaat      1080 cttacacat taaacatagt tctgtttttt gaaagttctt attttcattt ttatttgaat      1140
gttatatatt tttctatatt tataattcta gtaaaaggca aattttgctt ttaaatgaaa      1200
aaaatatata ttccacagtt tcacctaatc ttatgcattt agcagtacaa attcaaaaat      1260
ttcccatttt tattcatgaa tcataccatt atatattaac taaatccaag gtaaaaaaaa      1320
ggtatgaaag ctctatagta agtaaaaatat aaattcccca taaggaaagg gccaagtcca     1380
ccaggcaagt aaaatgagca agcaccactc caccatcaca caatttcact catagataac      1440
gataagattc atggaattat cttccacgtg gcattattcc agcggttcaa gccgataagg      1500
gtctcaacac ctctccttag gcctttgtgg ccgttaccaa gtaaaattaa cctcacacat      1560
atccacactc aaaatccaac ggtgtagatc ctagtccact tgaatctcat gtatcctaga      1620
ccctccgatc actccaaagc ttgttctcat tgttgttatc attatatata gatgaccaaa      1680
gcactagacc aaacct                                                      1696

<210> SEQ ID NO 15
<211> LENGTH: 1696
<212> TYPE: DNA
<213> ORGANISM: Zea mays

<400> SEQUENCE: 15
caaatttatt atgtgttttt tttccgtggt cgagattgtg tattattctt tagttattac       60 aagacttta gctaaaattt gaagaatttt acttaagaa aatcttaaca tctgagataa       120
tttcagcaat agattatatt tttcattact ctagcagtat ttttgcagat caatcgcaac      180
atatatggtt gttagaaaaa atgcactata tatatata ttattttttc aattaaaagt        240
gcatgatata taatatatat atatatatat atgtgtgtgt gtatatggtc aaagaaattc      300
ttatacaaat atacacgaac acatatattt gacaaaatca aagtattaca ctaaacaatg      360
agttggtgca tggccaaaac aaatatgtag attaaaaatt ccagcctcca aaaaaaaatc      420
caagtgttgt aaagcattat atatatatag tagatcccaa attttttgtac aattccacac     480 tgatcgaatt tttaaagttg aatatctgac gtaggatttt tttaatgtct tacctgacca      540
tttactaata acattcatac gttttcattt gaaatatcct ctataattat attgaatttg      600
gcacataata agaaacctaa ttggtgattt attttactag taaatttctg gtgatgggct      660
```

-continued

```
ttctactaga aagctctcgg aaaatcttgg accaaatcca tattccatga cttcgattgt      720
taaccctatt agttttcaca aacatactat caatatcatt gcaacggaaa aggtacaagt      780
aaaacattca atccgatagg gaagtgatgt aggaggttgg gaagacaggc ccagaaagag      840
atttatctga cttgttttgt gtatagtttt caatgttcat aaaggaagat ggagacttga      900 gaagttttt ttggactttg tttagctttg ttgggcgttt ttttttttga tcaataactt       960
tgttgggctt atgatttgta atattttcgt ggactcttta gtttatttag acgtgctaac     1020
tttgttgggc ttatgacttg ttgtaacata ttgtaacaga tgacttgatg tgcgactaat     1080
ctttacacat taaacatagt tctgtttttt gaaagttctt attttcattt ttatttgaat     1140
gttatatatt tttctatatt tataattcta gtaaaaggca aattttgctt ttaaatgaaa     1200
aaaatatata ttccacagtt tcacctaatc ttatgcattt agcagtacaa attcaaaaat     1260
ttcccatttt tattcatgaa tcataccatt atatattaac taaatccaag gtaaaaaaaa     1320
ggtatgaaag ctctatagta agtaaaatat aaattcccca taaggaaagg gccaagtcca     1380
ccaggcaagt aaaatgagca agcaccactc caccatcaca caatttcact catagataac     1440
gataagattc atggaattat cttccacgtg gcattattcc agcggttcaa gccgataagg     1500
gtctcaacac ctctccttag gcctttgtgg ccgttaccaa gtaaaattaa cctcacacat     1560
atccacactc aaaatccaac ggtgtagatc ctagtccact tgaatctcat gtatcctaga     1620
ccctccgatc actccaaagc ttgttctcat tgttgttatc attatatata gatgaccaaa     1680
gcactagacc aaacct                                                     1696
```

TRANSGENIC PLANTS WITH ENHANCED AGRONOMIC TRAITS

CROSS REFERENCE TO RELATED APPLICATIONS

This application claims benefit under 35 USC §119(e) of U.S. provisional application Ser. No. 60/638,099, filed Dec. 12, 2004, incorporated herein by reference.

INCORPORATION OF SEQUENCE LISTING

A sequence listing and a computer readable form (CRF) of the sequence listing, on CD-ROM, each containing the text file named "G1543C.ST25.txt", which is 63 KB (measured in MS-WINDOWS) and was created on Dec. 18, 2005, are herein incorporated by reference.

INCORPORATION OF COMPUTER LISTING

Appended hereto is a Computer Listing on duplicate CD-ROMs containing a folder labeled "hmmer-2.3.2" and two _.HMM files, incorporated herein by reference. Folder hmmer-2.3.2 contains the source code and other associated files for implementing the HMMer software for Pfam analysis. The _.HMM files contains Pfam Hidden Markov Models. The Computer Listings were created on Dec. 18, 2005.

FIELD OF THE INVENTION

Disclosed herein are inventions in the field of plant genetics and developmental biology. More specifically, the inventions provide plant cells with recombinant DNA for providing an enhanced trait in a transgenic plant, plants comprising such cells, seed and pollen derived from such plants, methods of making and using such cells, plants, seeds and pollen. In particular, the recombinant DNA of the inventions express transcription factors with homeobox domains.

BACKGROUND OF THE INVENTION

Transgenic plants with improved agronomic traits such as yield, environmental stress tolerance, pest resistance, herbicide tolerance, improved seed compositions, and the like are desired by both farmers and consumers. Although considerable efforts in plant breeding have provided significant gains in desired traits, the ability to introduce specific DNA into plant genomes provides further opportunities for generation of plants with improved and/or unique traits. Merely introducing recombinant DNA into a plant genome doesn't always produce a transgenic plant with an enhanced agronomic trait. Methods to select individual transgenic events from a population are required to identify those transgenic events that are characterized by the enhanced agronomic trait.

SUMMARY OF THE INVENTION

This invention employs recombinant DNA for expression of proteins that are useful for imparting enhanced agronomic traits to the transgenic plants. Recombinant DNA in this invention is provided in a construct comprising a promoter that is functional in plant cells and that is operably linked to DNA that encodes a protein having domains of amino acids in a sequence that exceed the Pfam gathering cutoff for amino acid sequence alignment with a Pfam Homeobox protein domain family and a Pfam HALZ protein domain family. The Pfam gathering cuttoff for the Homeobox protein domain family is −4 and the Pfam gathering cuttoff for the HALZ protein domain family is 17. Other aspects of the invention are specifically directed to transgenic plant cells comprising the recombinant DNA of the invention, transgenic plants comprising a plurality of such plant cells, progeny transgenic seed and transgenic pollen from such plants. Such plant cells are selected from a population of transgenic plants regenerated from plant cells transformed with recombinant DNA and that express the protein by screening transgenic plants in the population for an enhanced trait as compared to control plants that do not have said recombinant DNA, where the enhanced trait is selected from group of enhanced traits consisting of enhanced water use efficiency, enhanced cold tolerance, increased yield, enhanced nitrogen use efficiency, enhanced seed protein and enhanced seed oil.

In yet another aspect of the invention the plant cells, plants, seeds and pollen further comprise DNA expressing a protein that provides tolerance from exposure to an herbicide applied at levels that are lethal to a wild type of said plant cell. Such tolerance is especially useful not only as an advantageous trait in such plants but is also useful in a selection step in the methods of the invention. In aspects of the invention the agent of such herbicide is a glyphosate, dicamba, or glufosinate compound.

Yet other aspects of the invention provide transgenic plants which are homozygous for the recombinant DNA and transgenic seed of the invention from corn, soybean, cotton, canola, alfalfa, wheat or rice plants. In other important embodiments for practice of various aspects of the invention in Argentina the recombinant DNA is provided in plant cells derived from corn lines that that are and maintain resistance to the Mal de Rio Cuarto virus or the *Puccina sorghi* fungus or both.

This invention also provides methods for manufacturing non-natural, transgenic seed that can be used to produce a crop of transgenic plants with an enhanced trait resulting from expression of stably-integrated, recombinant DNA for expressing a protein selected from the group consisting of SEQ ID NO: 5-8. More specifically the method comprises (a) screening a population of plants for an enhanced trait and a recombinant DNA, where individual plants in the population can exhibit the trait at a level less than, essentially the same as or greater than the level that the trait is exhibited in control plants which do not express the recombinant DNA, (b) selecting from the population one or more plants that exhibit the trait at a level greater than the level that said trait is exhibited in control plants, (c) verifying that the recombinant DNA is stably integrated in said selected plants, (d) analyzing tissue of a selected plant to determine the production of a protein having the function of a protein encoded by nucleotides in a sequence of one of SEQ ID NO:1-4; and (e) collecting seed from a selected plant. In one aspect of the invention the plants in the population further comprise DNA expressing a protein that provides tolerance to exposure to an herbicide applied at levels that are lethal to wild type plant cells and the selecting is effected by treating the population with the herbicide, e.g. a glyphosate, dicamba, or glufosinate compound. In another aspect of the invention the plants are selected by identifying plants with the enhanced trait. The methods are especially useful for manufacturing corn, soybean, cotton, alfalfa, wheat or rice seed. In a another aspect, the plants further comprise a DNA expressing a second protein that provides plant cells with one or more enhanced agronomic traits.

Another aspect of the invention provides a method of producing hybrid corn seed comprising acquiring hybrid corn seed from a herbicide tolerant corn plant which also has stably-integrated, recombinant DNA comprising a promoter that is (a) functional in plant cells and (b) is operably linked to DNA that encodes a protein selected from the group consisting of SEQ ID NO: 5-8; wherein a progeny transgenic plant regenerated from a copy of said cell exhibits an enhanced trait as compared to a control plant without said DNA construct; and wherein said cell is selected from a population of cells transformed with said DNA construct by screening progeny plants of cells in said population for an enhanced trait as compared to said control plant, and wherein said enhanced trait is selected from the group consisting of enhanced water use efficiency, enhanced cold tolerance, increased yield, enhanced nitrogen use efficiency, enhanced seed protein and enhanced seed oil resulting from expression of said protein. The methods further comprise producing corn plants from said hybrid corn seed, wherein a fraction of the plants produced from said hybrid corn seed is homozygous for said recombinant DNA, a fraction of the plants produced from said hybrid corn seed is hemizygous for said recombinant DNA, and a fraction of the plants produced from said hybrid corn seed has none of said recombinant DNA; selecting corn plants which are homozygous and hemizygous for said recombinant DNA by treating with an herbicide; collecting seed from herbicide-treated-surviving corn plants and planting said seed to produce further progeny corn plants; repeating the selecting and collecting steps at least once to produce an inbred corn line; and crossing the inbred corn line with a second corn line to produce hybrid seed.

Another aspect of the invention provides a method of selecting a plant comprising plant cells of the invention by using an immunoreactive antibody to detect the presence of protein expressed by recombinant DNA in seed or plant tissue. Yet another aspect of the invention provides anti-counterfeit milled seed having, as an indication of origin, a plant cell of this invention.

Still other aspects of this invention relate to transgenic plants with enhanced water use efficiency or enhanced nitrogen use efficiency. For instance, this invention provides methods of growing a corn, cotton or soybean crop without irrigation water comprising planting seed having plant cells of the invention which are selected for enhanced water use efficiency. Alternatively methods comprise applying reduced irrigation water, e.g. providing up to 300 millimeters of ground water during the production of a corn crop. This invention also provides methods of growing a corn, cotton or soybean crop without added nitrogen fertilizer comprising planting seed having plant cells of the invention which are selected for enhanced nitrogen use efficiency.

DETAILED DESCRIPTION OF THE INVENTION

As used herein a "plant cell" means a plant cell that is transformed with stably-integrated, non-natural, recombinant DNA, e.g. by *Agrobacterium*-mediated transformation or by bombardment using microparticles coated with recombinant DNA or other means. A plant cell of this invention can be an originally-transformed plant cell that exists as a microorganism or as a progeny plant cell that is regenerated into differentiated tissue, e.g. into a transgenic plant with stably-integrated, non-natural recombinant DNA, or seed or pollen derived from a progeny transgenic plant.

As used herein a "transgenic plant" means a plant whose genome has been altered by the stable integration of recombinant DNA. A transgenic plant includes a plant regenerated from an originally-transformed plant cell and progeny transgenic plants from later generations or crosses of a transformed plant.

As used herein "recombinant DNA" means DNA which has been a genetically engineered and constructed outside of a cell including DNA containing naturally occurring DNA or cDNA or synthetic DNA.

As used herein "consensus sequence" means an artificial sequence of amino acids in a conserved region of an alignment of amino acid sequences of homologous proteins, e.g. as determined by a CLUSTALW alignment of amino acid sequence of homolog proteins.

As used herein "homolog" means a protein in a group of proteins that perform the same biological function, e.g. proteins that belong to the same Pfam protein family and that provide a common enhanced trait in transgenic plants of this invention. Homologs are expressed by homologous genes. Homologous genes include naturally occurring alleles and artificially-created variants. Degeneracy of the genetic code provides the possibility to substitute at least one base of the protein encoding sequence of a gene with a different base without causing the amino acid sequence of the polypeptide produced from the gene to be changed. Hence, a polynucleotide useful in the present invention may have any base sequence that has been changed from SEQ ID NO:1 through SEQ ID NO:4 by substitution in accordance with degeneracy of the genetic code. Homologs are proteins that, when optimally aligned, have at least 60% identity, more preferably about 70% or higher, more preferably at least 80% and even more preferably at least 90% identity over the full length of a protein identified as being associated with imparting an enhanced trait when expressed in plant cells. Homologs include proteins with an amino acid sequence that has at least 90% identity to a consensus amino acid sequence of proteins and homologs disclosed herein.

Homologs are be identified by comparison of amino acid sequence, e.g. manually or by use of a computer-based tool using known homology-based search algorithms such as those commonly known and referred to as BLAST, FASTA, and Smith-Waterman. A local sequence alignment program, e.g. BLAST, can be used to search a database of sequences to find similar sequences, and the summary Expectation value (E-value) used to measure the sequence base similarity. As a protein hit with the best E-value for a particular organism may not necessarily be an ortholog or the only ortholog, a reciprocal query is used in the present invention to filter hit sequences with significant E-values for ortholog identification. The reciprocal query entails search of the significant hits against a database of amino acid sequences from the base organism that are similar to the sequence of the query protein. A hit is a likely ortholog, when the reciprocal query's best hit is the query protein itself or a protein encoded by a duplicated gene after speciation. A further aspect of the invention comprises functional homolog proteins that differ in one or more amino acids from those of disclosed protein as the result of conservative amino acid substitutions, for example substitutions are among: acidic (negatively charged) amino acids such as aspartic acid and glutamic acid; basic (positively charged) amino acids such as arginine, histidine, and lysine; neutral polar amino acids such as glycine, serine, threonine, cysteine, tyrosine, asparagine, and glutamine; neutral nonpolar (hydrophobic) amino acids such as alanine, leucine, isoleucine, valine, proline, phenylalanine, tryptophan, and methionine; amino acids having aliphatic side chains such as glycine, alanine, valine, leucine, and isoleucine; amino acids having aliphatic-hydroxyl side chains such as serine and threonine; amino acids having amide-containing side chains such as asparagine and glutamine; amino acids having aromatic side chains such as phenylalanine, tyrosine, and tryptophan; amino acids having basic side chains such as lysine, arginine, and histidine; amino acids having sulfur-containing side chains such as cysteine and methionine; naturally conservative amino acids such as valine-leucine, valine-isoleucine, phenylalanine-tyrosine, lysine-arginine, alanine-valine, aspartic acid-glutamic acid, and asparagine-glutamine. A further aspect of the homologs encoded by DNA useful in the transgenic plants of the invention are those proteins that differ from a disclosed protein as the result of deletion or insertion of one or more amino acids in a native sequence.

As used herein, "percent identity" means the extent to which two optimally aligned DNA or protein segments are invariant throughout a window of alignment of components, for example nucleotide sequence or amino acid sequence. An "identity fraction" for aligned segments of a test sequence and a reference sequence is the number of identical components that are shared by sequences of the two aligned segments divided by the total number of sequence components in the reference segment over a window of alignment which is the smaller of the full test sequence or the full reference sequence. "Percent identity" ("% identity") is the identity fraction times 100.

As used herein "Pfam" refers to a large collection of multiple sequence alignments and hidden Markov models covering many common protein families, e.g. Pfam version 18.0 (August 2005) contains alignments and models for 7973 protein families and is based on the Swissprot 47.0 and SP-TrEMBL 30.0 protein sequence databases. See S. R. Eddy, "Profile Hidden Markov Models", *Bioinformatics* 14:755-763, 1998. Pfam is currently maintained and updated by a Pfam Consortium. The alignments represent some evolutionary conserved structure that has implications for the protein's function. Profile hidden Markov models (profile HMMs) built from the Pfam alignments are useful for automatically recognizing that a new protein belongs to an existing protein family even if the homology by alignment appears to be low. Once one DNA is identified as encoding a protein which imparts an enhanced trait when expressed in transgenic plants, other DNA encoding proteins in the same protein family are identified by querying the amino acid sequence of protein encoded by candidate DNA against the Hidden Markov Model which characterizes the Pfam domain using HMMER software, a current version of which is provided in the appended computer listing. Candidate proteins meeting the gathering cutoff for the alignment of a particular Pfam are in the protein family and have cognate DNA that is useful in constructing recombinant DNA for the use in the plant cells of this invention. Hidden Markov Model databases for use with HMMER software in identifying DNA expressing protein in a common Pfam for recombinant DNA in the plant cells of this invention are also included in the appended computer listing. The HMMER software and Pfam databases are version 18.0 and were used to determine that the amino acid sequence of SEQ ID NO:5 is characterized by two Pfam domains, i.e. Homeobox domain and HALZ domain. The Homeobox domain was identified as comprising amino acid residues between positions 130 and 193 with a score of 70.1 exceeding the gathering cutoff of −4. The HALZ domain was identified as comprising amino acid residues between positions 194 and 238 with a score of 71.9 exceeding the gathering cutoff of 17.

The HMMER software and databases for identifying the Homeobox and HALZ domains are accessed at any Pfam website and can be provided by the applicant, e.g. in an appended computer listing.

As used herein "promoter" means regulatory DNA for initializing transcription. A "plant promoter" is a promoter capable of initiating transcription in plant cells whether or not its origin is a plant cell, e.g. is it well known that *Agrobacterium* promoters are functional in plant cells. Thus, plant promoters include promoter DNA obtained from plants, plant viruses and bacteria such as *Agrobacterium* and *Bradyrhizobium* bacteria. Examples of promoters under developmental control include promoters that preferentially initiate transcription in certain tissues, such as leaves, roots, or seeds. Such promoters are referred to as "tissue preferred". Promoters that initiate transcription only in certain tissues are referred to as "tissue specific". A "cell type" specific promoter primarily drives expression in certain cell types in one or more organs, for example, vascular cells in roots or leaves. An "inducible" or "repressible" promoter is a promoter which is under environmental control. Examples of environmental conditions that may effect transcription by inducible promoters include anaerobic conditions, or certain chemicals, or the presence of light. Tissue specific, tissue preferred, cell type specific, and inducible promoters constitute the class of "non-constitutive" promoters. A "constitutive" promoter is a promoter which is active under most conditions.

As used herein "operably linked" means the association of two or more DNA fragments in a DNA construct so that the function of one, e.g. protein-encoding DNA, is controlled by the other, e.g. a promoter.

As used herein "expressed" means produced, e.g. a protein is expressed in a plant cell when its cognate DNA is transcribed to mRNA that is translated to the protein.

As used herein a "control plant" means a plant that does not contain the recombinant DNA that expressed a protein that impart an enhanced trait. A control plant is to identify and select a transgenic plant that has an enhance trait. A suitable control plant can be a non-transgenic plant of the parental line used to generate a transgenic plant, i.e. devoid of recombinant DNA. A suitable control plant may in some cases be a progeny of a hemizygous transgenic plant line that is does not contain the recombinant DNA, known as a negative segregant.

As used herein an "enhanced trait" means a characteristic of a transgenic plant that includes, but is not limited to, an enhance agronomic trait characterized by enhanced plant morphology, physiology, growth and development, yield, nutritional enhancement, disease or pest resistance, or environmental or chemical tolerance. In more specific aspects of this invention enhanced trait is selected from group of enhanced traits consisting of enhanced water use efficiency, enhanced cold tolerance, increased yield, enhanced nitrogen use efficiency, enhanced seed protein and enhanced seed oil. In an important aspect of the invention the enhanced trait is enhanced yield including increased yield under non-stress conditions and increased yield under environmental stress conditions. Stress conditions may include, for example, drought, shade, fungal disease, viral disease, bacterial disease, insect infestation, nematode infestation, cold temperature exposure, heat exposure, osmotic stress, reduced nitrogen nutrient availability, reduced phosphorus nutrient availability and high plant density. "Yield" can be affected by many properties including without limitation, plant height, pod number, pod position on the plant, number of internodes, incidence of pod shatter, grain size, efficiency of nodulation and nitrogen fixation, efficiency of nutrient assimilation, resistance to biotic and abiotic stress, carbon assimilation, plant architecture, resistance to lodging, percent seed germination, seedling vigor, and juvenile traits. Yield can also affected by efficiency of germination (including germination in stressed conditions), growth rate (including growth rate in stressed conditions), ear number, seed number per ear, seed size, composition of seed (starch, oil, protein) and characteristics of seed fill.

Increased yield of a transgenic plant of the present invention can be measured in a number of ways, including test weight, seed number per plant, seed weight, seed number per unit area (i.e. seeds, or weight of seeds, per acre), bushels per acre (bu/a), tonnes per acre, tons per acre, kilo per hectare. For example, maize yield may be measured as production of shelled corn kernels per unit of production area, for example in bushels per acre or metric tons per hectare, often reported on a moisture adjusted basis, for example at 15.5 percent moisture. Increased yield may result from improved utilization of key biochemical compounds, such as nitrogen, phosphorous and carbohydrate, or from improved responses to environmental stresses, such as cold, heat, drought, salt, and attack by pests or pathogens. Recombinant DNA used in this invention can also be used to provide plants having improved growth and development, and ultimately increased yield, as the result of modified expression of plant growth regulators or modification of cell cycle or photosynthesis pathways. Also of interest is the generation of transgenic plants that demonstrate enhanced yield with respect to a seed component that may or may not correspond to an increase in overall plant yield. Such properties include enhancements in seed oil, seed molecules such as tocopherol, protein and starch, or oil particular oil components as may be manifest by an alteration in the ratios of seed components.

A subset of the nucleic molecules of this invention includes fragments of the disclosed recombinant DNA consisting of oligonucleotides of at least 15, preferably at least 16 or 17, more preferably at least 18 or 19, and even more preferably at least 20 or more, consecutive nucleotides. Such oligonucleotides are fragments of the larger molecules having a sequence selected from the group consisting of SEQ ID NO: 1 through SEQ ID NO:4, and find use, for example as probes and primers for detection of the polynucleotides of the present invention.

DNA constructs are assembled using methods well known to persons of ordinary skill in the art and typically comprise a promoter operably linked to DNA, the expression of which provides the enhanced agronomic trait. Other construct components may include additional regulatory elements, such as 5' leaders and introns for enhancing transcription, 3' untranslated regions (such as polyadenylation signals and sites), DNA for transit or signal peptides.

Numerous promoters that are active in plant cells have been described in the literature. These include promoters present in plant genomes as well as promoters from other sources, including nopaline synthase (NOS) promoter and octopine synthase (OCS) promoters carried on tumor-inducing plasmids of *Agrobacterium tumefaciens, caulimovirus* promoters such as the cauliflower mosaic virus. For instance, see U.S. Pat. Nos. 5,858,742 and 5,322,938, which disclose versions of the constitutive promoter derived from cauliflower mosaic virus (CaMV35S), U.S. Pat. No. 5,641,876, which discloses a rice actin promoter, U.S. Patent Application Publication 2002/0192813A1, which discloses 5', 3' and intron elements useful in the design of effective plant expression vectors, U.S. patent application Ser. No. 09/757,089, which discloses a maize chloroplast aldolase promoter, U.S. patent application Ser. No. 08/706,946, which discloses a rice glutelin promoter, U.S. patent application Ser. No. 09/757,089, which discloses a maize aldolase (FDA) promoter, and U.S. patent application Ser. No. 60/310,370, which discloses a maize nicotianamine synthase promoter, all of which are incorporated herein by reference. These and numerous other promoters that function in plant cells are known to those skilled in the art and available for use in recombinant polynucleotides of the present invention to provide for expression of desired genes in transgenic plant cells.

In other aspects of the invention, preferential expression in plant green tissues is desired. Promoters of interest for such uses include those from genes such as *Arabidopsis thaliana* ribulose-1,5-bisphosphate carboxylase (Rubisco) small subunit (Fischhoff et al. (1992) Plant Mol Biol. 20:81-93), aldolase and pyruvate orthophosphate dikinase (PPDK) (Taniguchi et al. (2000) *Plant Cell Physiol.* 41(1):42-48).

Furthermore, the promoters may be altered to contain multiple "enhancer sequences" to assist in elevating gene expression. Such enhancers are known in the art. By including an enhancer sequence with such constructs, the expression of the selected protein may be enhanced. These enhancers often are found 5' to the start of transcription in a promoter that functions in eukaryotic cells, but can often be inserted upstream (5') or downstream (3') to the coding sequence. In some instances, these 5' enhancing elements are introns. Particularly useful as enhancers are the 5' introns of the rice actin 1 (see U.S. Pat. No. 5,641,876) and rice actin 2 genes, the maize alcohol dehydrogenase gene intron, the maize heat shock protein 70 gene intron (U.S. Pat. No. 5,593,874) and the maize shrunken 1 gene.

In other aspects of the invention, sufficient expression in plant seed tissues is desired to effect improvements in seed composition. Exemplary promoters for use for seed composition modification include promoters from seed genes such as napin (U.S. Pat. No. 5,420,034), maize L3 oleosin (U.S. Pat. No. 6,433,252), zein Z27 (Russell et al. (1997) *Transgenic Res.* 6(2):157-166), globulin 1 (Belanger et al (1991) Genetics 129:863-872), glutelin 1 (Russell (1997) supra), and peroxiredoxin antioxidant (Per1) (Stacy et al. (1996) *Plant Mol Biol.* 31(6):1205-1216).

Recombinant DNA constructs prepared in accordance with the invention will also generally include a 3' element that typically contains a polyadenylation signal and site. Well-known 3' elements include those from *Agrobacterium tumefaciens* genes such as nos 3', tml 3', tmr 3', tms 3', ocs 3', tr73', for example disclosed in U.S. Pat. No. 6,090,627, incorporated herein by reference; 3' elements from plant genes such as wheat (*Triticum aesevitum*) heat shock protein 17 (Hsp17 3'), a wheat ubiquitin gene, a wheat fructose-1,6-biphosphatase gene, a rice glutelin gene a rice lactate dehydrogenase gene and a rice beta-tubulin gene, all of which are disclosed in U.S. published patent application 2002/0192813 A1, incorporated herein by reference; and the pea (*Pisum sativum*) ribulose biphosphate carboxylase gene (rbs 3'), and 3' elements from the genes within the host plant.

Constructs and vectors may also include a transit peptide for targeting of a gene target to a plant organelle, particularly to a chloroplast, leucoplast or other plastid organelle. For descriptions of the use of chloroplast transit peptides see U.S. Pat. No. 5,188,642 and U.S. Pat. No. 5,728,925, incorporated herein by reference. For description of the transit peptide region of an Arabidopsis EPSPS gene useful in the present invention, see Klee, H. J. et al (MGG (1987) 210:437-442).

Transgenic plants comprising or derived from plant cells of this invention transformed with recombinant DNA can be further enhanced with stacked traits, e.g. a crop plant having an enhanced trait resulting from expression of DNA disclosed herein in combination with herbicide and/or pest resistance traits. For example, genes of the current invention can be stacked with other traits of agronomic interest, such as a trait providing herbicide resistance, or insect resistance, such as using a gene from *Bacillus thuringensis* to provide resistance against lepidopteran, coliopteran, homopteran, hemiopteran, and other insects. Herbicides for which transgenic plant tolerance has been demonstrated and the method of the present invention can be applied include, but are not limited to, glyphosate, dicamba, glufosinate, sulfonylurea, bromoxynil and norflurazon herbicides. Polynucleotide molecules encoding proteins involved in herbicide tolerance are well-known in the art and include, but are not limited to, a polynucleotide molecule encoding 5-enolpyruvylshikimate-3-phosphate synthase (EPSPS) disclosed in U.S. Pat. Nos. 5,094,945; 5,627,061; 5,633,435 and 6,040,497 for imparting glyphosate tolerance; polynucleotide molecules encoding a glyphosate oxidoreductase (GOX) disclosed in U.S. Pat. No. 5,463,175 and a glyphosate-N-acetyl transferase (GAT) disclosed in U.S. Patent Application publication 2003/0083480 A1 also for imparting glyphosate tolerance; dicamba monooxygenase disclosed in U.S. Patent Application publication 2003/0135879 A1 for imparting dicamba tolerance; a polynucleotide molecule encoding bromoxynil nitrilase (Bxn) disclosed in U.S. Pat. No. 4,810,648 for imparting bromoxynil tolerance; a polynucleotide molecule encoding phytoene desaturase (crtI) described in Misawa et al, (1993) *Plant J.* 4:833-840 and Misawa et al, (1994) *Plant J.* 6:481-489 for norflurazon tolerance; a polynucleotide molecule encoding acetohydroxyacid synthase (AHAS, aka ALS) described in Sathasiivan et al. (1990) *Nucl. Acids Res.* 18:2188-2193 for imparting tolerance to sulfonylurea herbicides; polynucleotide molecules known as bar genes disclosed in DeBlock, et al. (1987) *EMBO J.* 6:2513-2519 for imparting glufosinate and bialaphos tolerance; polynucleotide molecules disclosed in U.S. Patent Application Publication 2003/010609 A1 for imparting N-amino methyl phosphonic acid tolerance; polynucleotide molecules disclosed in U.S. Pat. No. 6,107,549 for impartinig pyridine herbicide resistance; molecules and methods for imparting tolerance to multiple herbicides such as glyphosate, atrazine, ALS inhibitors, isoxoflutole and glufosinate herbicides are disclosed in U.S. Pat. No. 6,376,754 and U.S. Patent Application Publication 2002/0112260, all of said U.S. Patents and Patent Application Publications are incorporated herein by reference. Molecules and methods for imparting insect/nematode/virus resistance are disclosed in U.S. Pat. Nos. 5,250,515; 5,880,275; 6,506,599; 5,986,175 and U.S. Patent Application Publication 2003/0150017 A1, all of which are incorporated herein by reference.

In particular embodiments, the inventors contemplate the use of antibodies, either monoclonal or polyclonal which bind to the proteins disclosed herein. Means for preparing and characterizing antibodies are well known in the art (See, e.g., Antibodies: A Laboratory Manual, Cold Spring Harbor Laboratory, 1988; incorporated herein by reference). The methods for generating monoclonal antibodies (mAbs) generally begin along the same lines as those for preparing polyclonal antibodies. Briefly, a polyclonal antibody is prepared by immunizing an animal with an immunogenic composition in accordance with the present invention and collecting antisera from that immunized animal. A wide range of animal species can be used for the production of antisera. Typically the animal used for production of anti-antisera is a rabbit, a mouse, a rat, a hamster, a guinea pig or a goat. Because of the relatively large blood volume of rabbits, a rabbit is a preferred choice for production of polyclonal antibodies.

As is well known in the art, a given composition may vary in its immunogenicity. It is often necessary therefore to boost the host immune system, as may be achieved by coupling a peptide or polypeptide immunogen to a carrier. Exemplary and preferred carriers are keyhole limpet hemocyanin (KLH) and bovine serum albumin (BSA). Other albumins such as ovalbumin, mouse serum albumin or rabbit serum albumin can also be used as carriers. Means for conjugating a polypeptide to a carrier protein are well known in the art and include using glutaraldehyde, m-maleimidobencoyl-N-hydroxysuccinimide ester, carbodiimide and bis-biazotized benzidine.

As is also well known in the art, the immunogenicity of a particular immunogen composition can be enhanced by the use of non-specific stimulators of the immune response, known as adjuvants. Exemplary and preferred adjuvants include complete Freund's adjuvant (a non-specific stimulator of the immune response containing killed *Mycobacterium tuberculosis*), incomplete Freund's adjuvants and aluminum hydroxide adjuvant.

The amount of immunogen composition used in the production of polyclonal antibodies varies upon the nature of the immunogen as well as the animal used for immunization. A variety of routes can be used to administer the immunogen (subcutaneous, intramuscular, intradermal, intravenous and intraperitoneal). The production of polyclonal antibodies may be monitored by sampling blood of the immunized animal at various points following immunization. A second, booster, injection may also be given. The process of boosting and titering is repeated until a suitable titer is achieved. When a desired level of immunogenicity is obtained, the immunized animal can be bled and the serum isolated and stored, and/or the animal can be used to generate mAbs.

mAbs may be readily prepared through use of well-known techniques, such as those exemplified in U.S. Pat. No. 4,196,265, incorporated herein by reference. Typically, this technique involves immunizing a suitable animal with a selected immunogen composition, e.g., a purified or partially purified antifungal protein, polypeptide or peptide. The immunizing composition is administered in a manner effective to stimulate antibody producing cells. Rodents such as mice and rats are preferred animals, however, the use of rabbit, sheep, or frog cells is also possible. The use of rats may provide certain advantages (Goding, 1986, pp. 60-61), but mice are preferred, with the BALB/c mouse being most preferred as this is most routinely used and generally gives a higher percentage of stable fusions.

Following immunization, somatic cells with the potential for producing antibodies, specifically B lymphocytes (B cells), are selected for use in the mAb generating protocol. These cells may be obtained from biopsied spleens, tonsils or lymph nodes, or from a peripheral blood sample. Spleen cells and peripheral blood cells are preferred, the former because they are a rich source of antibody-producing cells that are in the dividing plasmablast stage, and the latter because peripheral blood is easily accessible. Often, a panel of animals will have been immunized and the spleen of animal with the highest antibody titer will be removed and the spleen lymphocytes obtained by homogenizing the spleen with a syringe. Typically, a spleen from an immunized mouse contains approximately $5\times10^7$ to $2\times10^8$ lymphocytes.

The antibody-producing B lymphocytes from the immunized animal are then fused with cells of an immortal myeloma cell, generally one of the same species as the animal that was immunized. Myeloma cell lines suited for use in hybridoma-producing fusion procedures preferably are non-antibody-producing, have high fusion efficiency, and enzyme deficiencies that render them incapable of growing in certain selective media which support the growth of only the desired fused cells (hybridomas).

Any one of a number of myeloma cells may be used, as are known to those of skill in the art (Goding, 1986, pp. 65-66; Campbell, 1984, pp. 75-83). For example, where the immunized animal is a mouse, one may use P3-X63/Ag8, X63-

Ag8.653, NS1/1.Ag 4 1, Sp210-Ag14, FO, NSO/U, MPC-11, MPC11-X45-GTG 1.7 and S194/5XX0 Bul; for rats, one may use R210.RCY3, Y3-Ag 1.2.3, IR983F and 4B210; and U-266, GM1500-GRG2, LICR-LON-HMy2 and UC729-6 are all useful in connection with human cell fusions.

One preferred murine myeloma cell is the NS-1 myeloma cell line (also termed P3-NS-1-Ag4-1), which is readily available from the NIGMS Human Genetic Mutant Cell Repository by requesting cell line repository number GM3573. Another mouse myeloma cell line that may be used is the 8-azaguanine-resistant mouse murine myeloma SP2/0 non-producer cell line.

Methods for generating hybrids of antibody-producing spleen or lymph node cells and myeloma cells usually comprise mixing somatic cells with myeloma cells in a 2:1 ratio, though the ratio may vary from about 20:1 to about 1:1, respectively, in the presence of an agent or agents (chemical or electrical) that promote the fusion of cell membranes. Fusion methods using Spend virus have been described (Kohler and Milstein, 1975; 1976), and those using polyethylene glycol (PEG), such as 37% (v/v) PEG, (Gefter et al., 1977). The use of electrically induced fusion methods is also appropriate (Goding, 1986, pp. 71-74).

Fusion procedures usually produce viable hybrids at low frequencies, about $1\times10^{-6}$ to $1\times10^{-8}$. However, this does not pose a problem, as the viable, fused hybrids are differentiated from the parental, unfused cells (particularly the unfused myeloma cells that would normally continue to divide indefinitely) by culturing in a selective medium. The selective medium is generally one that contains an agent that blocks the de novo synthesis of nucleotides in the tissue culture media. Exemplary and preferred agents are aminopterin, methotrexate, and azaserine. Aminopterin and methotrexate block de novo synthesis of both purines and pyrimidines, whereas azasenne blocks only purine synthesis. Where aminopterin or methotrexate is used, the media is supplemented with hypoxanthine and thymidine as a source of nucleotides (HAT medium). Where azaserine is used, the media is supplemented with hypoxanthine.

The preferred selection medium is HAT. Only cells capable of operating nucleotide salvage pathways are able to survive in HAT medium. The myeloma cells are defective in key enzymes of the salvage pathway, e.g., hypoxanthine phosphoribosyl transferase (HPRT), and they cannot survive. The B-cells can operate this pathway, but they have a limited life span in culture and generally die within about two weeks. Therefore, the only cells that can survive in the selective media are those hybrids formed from myeloma and B-cells.

This culturing provides a population of hybridomas from which specific hybridomas are selected. Typically, selection of hybridomas is performed by culturing the cells by single-clone dilution in microtiter plates, followed by testing the individual clonal supernatants (after about two to three weeks) for the desired reactivity. The assay should be sensitive, simple and rapid, such as radioimmunoassays, enzyme immunoassays, cytotoxicity assays, plaque assays, dot immunobinding assays, and the like.

The selected hybridomas would then be serially diluted and cloned into individual antibody-producing cell lines, which clones can then be propagated indefinitely to provide mAbs. The cell lines may be exploited for mAb production in two basic ways. A sample of the hybridoma can be injected (often into the peritoneal cavity) into a histocompatible animal of the type that was used to provide the somatic and myeloma cells for the original fusion. The injected animal develops tumors secreting the specific monoclonal antibody produced by the fused cell hybrid. The body fluids of the animal, such as serum or ascites fluid, can then be tapped to provide mAbs in high concentration. The individual cell lines could also be cultured in vitro, where the mAbs are naturally secreted into the culture medium from which they can be readily obtained in high concentrations. mAbs produced by either means may be further purified, if desired, using filtration, centrifugation and various chromatographic methods such as HPLC or affinity chromatography.

Plant Cell Transformation Methods

Numerous methods for transforming plant cells with recombinant DNA are known in the art and may be used in the present invention. Two commonly used methods for plant transformation are *Agrobacterium*-mediated transformation and microprojectile bombardment. Microprojectile bombardment methods are illustrated in U.S. Pat. No. 5,015,580 (soybean); U.S. Pat. No. 5,550,318 (corn); U.S. Pat. No. 5,538,880 (corn); U.S. Pat. No. 5,914,451 (soybean); U.S. Pat. No. 6,160,208 (corn); U.S. Pat. No. 6,399,861 (corn) and U.S. Pat. No. 6,153,812 (wheat) and *Agrobacterium*-mediated transformation is described in U.S. Pat. No. 5,159,135 (cotton); U.S. Pat. No. 5,824,877 (soybean); U.S. Pat. No. 5,591,616 (corn); and U.S. Pat. No. 6,384,301 (soybean), all of which are incorporated herein by reference. For *Agrobacterium tumefaciens* based plant transformation system, additional elements present on transformation constructs will include T-DNA left and right border sequences to facilitate incorporation of the recombinant polynucleotide into the plant genome.

In general it is useful to introduce recombinant DNA randomly, i.e. at a non-specific location, in the genome of a target plant line. In special cases it may be useful to target recombinant DNA insertion in order to achieve site-specific integration, for example to replace an existing gene in the genome, to use an existing promoter in the plant genome, or to insert a recombinant polynucleotide at a predetermined site known to be active for gene expression. Several site specific recombination systems exist which are known to function implants include cre-lox as disclosed in U.S. Pat. No. 4,959,317 and FLP-FRT as disclosed in U.S. Pat. No. 5,527,695, both incorporated herein by reference.

Transformation methods of this invention are preferably practiced in tissue culture on media and in a controlled environment. "Media" refers to the numerous nutrient mixtures that are used to grow cells in vitro, that is, outside of the intact living organism. Recipient cell targets include, but are not limited to, meristem cells, callus, immature embryos and gametic cells such as microspores, pollen, sperm and egg cells. It is contemplated that any cell from which a fertile plant may be regenerated is useful as a recipient cell. Callus may be initiated from tissue sources including, but not limited to, immature embryos, seedling apical meristems, microspores and the like. Cells capable of proliferating as callus are also recipient cells for genetic transformation. Practical transformation methods and materials for making transgenic plants of this invention, for example various media and recipient target cells, transformation of immature embryo cells and subsequent regeneration of fertile transgenic plants are disclosed in U.S. Pat. Nos. 6,194,636 and 6,232,526, which are incorporated herein by reference.

The seeds of transgenic plants can be harvested from fertile transgenic plants and be used to grow progeny generations of transformed plants of this invention including hybrid plants line for selection of plants having an enhanced trait. In addition to direct transformation of a plant with a recombinant DNA, transgenic plants can be prepared by crossing a first plant having a recombinant DNA with a second plant lacking the DNA. For example, recombinant DNA can be introduced into first plant line that is amenable to transformation to produce a transgenic plant which can be crossed with a second plant line to introgress the recombinant DNA into the second plant line. A transgenic plant with recombinant DNA providing an enhanced trait, e.g. enhanced yield, can be crossed with transgenic plant line having other recombinant DNA that confers another trait, for example herbicide resistance or pest resistance, to produce progeny plants having recombinant DNA that confers both traits. Typically, in such breeding for combining traits the transgenic plant donating the additional trait is a male line and the transgenic plant carrying the base traits is the female line. The progeny of this cross will segregate such that some of the plants will carry the DNA for both parental traits and some will carry DNA for one parental trait; such plants can be identified by markers associated with parental recombinant DNA, e.g. marker identification by analysis for recombinant DNA or, in the case where a selectable marker is linked to the recombinant, by application of the selecting agent such as a herbicide for use with a herbicide tolerance marker, or by selection for the enhanced trait. Progeny plants carrying DNA for both parental traits can be crossed back into the female parent line multiple times, for example usually 6 to 8 generations, to produce a progeny plant with substantially the same genotype as one original transgenic parental line but for the recombinant DNA of the other transgenic parental line In the practice of transformation DNA is typically introduced into only a small percentage of target plant cells in any one transformation experiment. Marker genes are used to provide an efficient system for identification of those cells that are stably transformed by receiving and integrating a transgenic DNA construct into their genomes. Preferred marker genes provide selective markers which confer resistance to a selective agent, such as an antibiotic or herbicide. Any of the herbicides to which plants of this invention may be resistant are useful agents for selective markers. Potentially transformed cells are exposed to the selective agent. In the population of surviving cells will be those cells where, generally, the resistance-conferring gene is integrated and expressed at sufficient levels to permit cell survival. Cells may be tested further to confirm stable integration of the exogenous DNA. Commonly used selective marker genes include those conferring resistance to antibiotics such as kanamycin and paromomycin (nptII), hygromycin B (aph IV) and gentamycin (aac3 and aacC4) or resistance to herbicides such as glufosinate (bar or pat) and glyphosate (aroA or EPSPS). Examples of such selectable are illustrated in U.S. Pat. Nos. 5,550,318; 5,633,435; 5,780,708 and 6,118,047, all of which are incorporated herein by reference. Selectable markers which provide an ability to visually identify transformants can also be employed, for example, a gene expressing a colored or fluorescent protein such as a luciferase or green fluorescent protein (GFP) or a gene expressing a beta-glucuronidase or uidA gene (GUS) for which various chromogenic substrates are known.

Plant cells that survive exposure to the selective agent, or plant cells that have been scored positive in a screening assay, may be cultured in regeneration media and allowed to mature into plants. Developing plantlets regenerated from transformed plant cells can be transferred to plant growth mix, and hardened off, for example, in an environmentally controlled chamber at about 85% relative humidity, 600 ppm $CO_2$, and 25-250 microeinsteins $m^{-2}$ $s^{-1}$ of light, prior to transfer to a greenhouse or growth chamber for maturation. Plants are regenerated from about 6 weeks to 10 months after a transformant is identified, depending on the initial tissue. Plants may be pollinated using conventional plant breeding methods known to those of skill in the art and seed produced, for example self-pollination is commonly used with transgenic corn. The regenerated transformed plant or its progeny seed or plants can be tested for expression of the recombinant DNA and selected for the presence of enhanced agronomic trait.

Transgenic Plants and Seeds

Transgenic plants derived from the plant cells of this invention are grown to generate transgenic plants having an enhanced trait as compared to a control plant and produce transgenic seed and haploid pollen of this invention. Such plants with enhanced traits are identified by selection of transformed plants or progeny seed for the enhanced trait. For efficiency a selection method is designed to evaluate multiple transgenic plants (events) comprising the recombinant DNA, for example multiple plants from 2 to 20 or more transgenic events. Transgenic plants grown from transgenic seed provided herein demonstrate improved agronomic traits that contribute to increased yield or other trait that provides increased plant value, including, for example, improved seed quality. Of particular interest are plants having enhanced water use efficiency, enhanced cold tolerance, increased yield, enhanced nitrogen use efficiency, enhanced seed protein and enhanced seed oil.

Table 1 provides a list of protein encoding DNA ("genes") that are useful as recombinant DNA for production of transgenic plants with enhanced agronomic trait, the elements of Table 1 are described by reference to:

"PEP SEQ" which identifies an amino acid sequence from SEQ ID NO:5-8.

"NUC SEQ" which identifies a DNA sequence from SEQ ID NO:1-4.

"Base Vector" which identifies a base plasmid used for transformation of the recombinant DNA.

"PROTEIN NAME" which is a common name for protein encoded by the recombinant DNA.

"Plasmid ID" which identifies an arbitrary name for the plant transformation plasmid comprising recombinant DNA for expressing the recombinant DNA in plant cells.

TABLE 1

| PEP SEQ ID NO | NUC SEQ ID NO | Base Vector | PROTEIN NAME | Plasmid ID |
|---|---|---|---|---|
| 5 | 1 | pMON65154 | *Arabidopsis* G1543 | pMON68392 |
| 5 | 1 | | *Arabidopsis* G1543 | pMON74775 |
| 5 | 1 | pMON74537 | *Arabidopsis* G1543 | pMON83062 |
| 6 | 2 | pMON81244 | Corn G1543-like 1 | pMON82686 |
| 6 | 2 | pMON74537 | Corn G1543-like 1 | pMON83049 |
| 7 | 3 | pMON81244 | Soy G1543-like 1 | pMON82688 |
| 7 | 3 | pMON81244 | Soy G1543-like 1 | pMON84131 |
| 7 | 3 | pMON74537 | Soy G1543-like 1 | pMON83311 |
| 8 | 4 | pMON74537 | rice Hox3-AAD37696 | pMON73829 |

Screening Methods for Transgenic Plants with Enhanced Agronomic Trait

Many transgenic events which survive to fertile transgenic plants that produce seeds and progeny plants will not exhibit an enhanced agronomic trait. Screening is necessary to identify the transgenic plant of this invention. Transgenic plants having enhanced argonomic traits are identified from populations of plants transformed as described herein by evaluating the trait in a variety of assays to detect an enhanced agronomic trait. These assays also may take many forms, including but not limited to, analyses to detect changes in the chemical composition, biomass, physiological properties, morphology of the plant. Changes in chemical compositions such as nutritional composition of grain can be detected by analysis of the seed composition and content of protein, free amino acids, oil, free fatty acids, starch or tocopherols. Changes in biomass characteristics can be made on greenhouse or field grown plants and can include plant height, stem diameter, root and shoot dry weights; and, for corn plants, ear length and diameter. Changes in physiological properties can be identified by evaluating responses to stress conditions, e.g., assays using imposed stress conditions such as water deficit, nitrogen deficiency, cold growing conditions, pathogen or insect attack or light deficiency, or increased plant density. Changes in morphology can be measured by visual observation of tendency of a transformed plant with an enhanced agronomic trait to also appear to be a normal plant as compared to changes toward bushy, taller, thicker, narrower leaves, striped leaves, knotted trait, chlorosis, albino, anthocyanin production, or altered tassels, ears or roots. Other screening properties include days to pollen shed, days to silking, leaf extension rate, chlorophyll content, leaf temperature, stand, seedling vigor, internode length, plant height, leaf number, leaf area, tillering, brace roots, stay green, stalk lodging, root lodging, plant health, barreness/prolificacy, green snap, and pest resistance. In addition, phenotypic characteristics of harvested grain may be evaluated, including number of kernels per row on the ear, number of rows of kernels on the ear, kernel abortion, kernel weight, kernel size, kernel density and physical grain quality.

Although preferred seeds for transgenic plants with enhanced agronomic traits of this invention are corn and soybean plants, other seeds are for cotton, canola, wheat, sunflower, sorghum, alfalfa, barley, millet, rice, tobacco, fruit and vegetable crops, and turfgrass.

Screening for Enhanced Nitrogen Use Efficiency

One preferred enhanced agronomic trait in transgenic plants of this invention is enhanced nitrogen use efficiency as compared to control plants. Higher nitrogen soil applications increase seed protein and starch accumulation, and lead to larger seed weight and larger-kernel number per ear. Recent improvements in elite high yielding corn hybrid genotypes include the ability to utilize nitrogen efficiently. Genes causing the enhanced nitrogen use efficiency in crop plants are especially useful, e.g., for improving yield. Enhanced nitrogen use efficiency can be assessed by measuring changes in plant growth such as leaf area production, shoot biomass, chlorophyll content in plants grown in nitrogen limiting conditions and/or nitrogen sufficient conditions. It is useful to conduct a first screen in nitrogen limiting conditions and confirm replicate transgenic events in both nitrogen limiting and nitrogen sufficient conditions. Table 2 shows the amount of nutrients in the nutrient solution for nitrogen limiting conditions (low nitrogen growth condition) and nitrogen sufficient conditions (high nitrogen growth condition) useful for nitrogen use efficiency screening. For example in a greenhouse screen pots of transgenic plants and control plants are treated with 100 ml of nutrient solution three times a week on alternate days starting at 8 and 10 days after planting for high nitrogen and low nitrogen screening, respectively.

TABLE 2

| Nutrient Stock | 2 mM $NH_4NO_3$ (low Nitrogen growth condition) mL/L | 20 mM $NH_4NO_3$ (high Nitrogen growth condition) mL/L |
|---|---|---|
| 1 M $NH_4NO_3$ | 2 | 20 |
| 1 M $KH_2PO_4$ | 0.5 | 0.5 |
| 1 M $MgSO_4.7H_2O$ | 2 | 2 |
| 1 M $CaCl_2$ | 2.5 | 2.5 |
| 1 M $K_2SO_4$ | 1 | 1 |

Note:
Adjust pH to 5.6 with HCl or KOH

After 28 days of plant growth for low nitrogen screening and 23 days for high nitrogen screening, measurements are taken for: total shoot fresh mass, leaf chlorophyll, leaf area, leaf fresh mass and leaf dry mass.

Screening for Increased Yield

Many transgenic plants of this invention exhibit enhanced yield as compared to a control plant. Enhanced yield can result from enhanced seed sink potential, i.e. the number and size of endosperm cells or kernels and/or enhanced sink strength, i.e. the rate of starch biosynthesis. Sink potential can be established very early during kernel development, as endosperm cell number and cell size are determined within the first few days after pollination.

Much of the increase in corn yield of the past several decades has resulted from an increase in planting density. During that period, corn yield has been increasing at a rate of 2.1 bushels/acre/year, but the planting density has increased at a rate of 250 plants/acre/year. A characteristic of modern hybrid corn is the ability of these varieties to be planted at high density. Many studies have shown that a higher than current planting density should result in more biomass production, but current germplasm does not perform well at these higher densities. One approach to increasing yield is to increase harvest index (HI), the proportion of biomass that is allocated to the kernel compared to total biomass, in high density plantings.

Effective yield screening of transgenic corn uses hybrid progeny of the transgenic event over multiple locations with plants grown under optimal production management practices, and maximum pest control. A useful target for enhanced yield is a 5% to 10% increase in yield as compared to yield produced by plants grown from seed for a control plant. Useful screening in multiple and diverse geographic locations, e.g., up to 16 or more locations, over one or more plating seasons, e.g., at least two planting seasons to statistically distinguish yield improvement from natural environmental effects. It is to plant multiple transgenic plants, positive and negative control plants, and pollinator plants in standard plots, e.g., 2 row plots, 20 feet long by 5 feet wide with 30 inches distance between rows and a 3 foot alley between ranges. Transgenic events can be grouped by recombinant DNA constructs with groups randomly placed in the field. A pollinator plot of a high quality corn line is planted for every two plots to allow open pollination when using male sterile transgenic events. A useful planting density is about 30,000 plants/acre.

Surrogate indicators for screening for yield improvement include source capacity (biomass), source output (sucrose and photosynthesis), sink components (kernel size, ear size, starch in the seed), development (light response, height, density tolerance), maturity, early flowering trait and physiological responses to high density planting, e.g., at 45,000 plants per acre, e.g., as illustrated in Table 3 and 4.

TABLE 3

| Timing | Evaluation | Description | comments |
|---|---|---|---|
| V2-3 | Early stand | Can be taken any time after germination and prior to removal of any plants. | |
| Pollen shed | GDU to 50% shed | GDU to 50% plants shedding 50% tassel. | |
| Silking | GDU to 50% silk | GDU to 50% plants showing silks. | |

TABLE 3-continued

| Timing | Evaluation | Description | comments |
|---|---|---|---|
| Maturity | Plant height | Height from soil surface to flag leaf attachment (inches). | 10 plants per plot - Yield team assistance |
| Maturity | Ear height | Height from soil surface to primary ear attachment node. | 10 plants per plot - Yield team assistance |
| Maturity | Leaves above ear | visual scores: erect, size, rolling | |
| Maturity | Tassel size | Visual scores +/− vs. WT | |
| Pre-Harvest | Final Stand | Final stand count prior to harvest, exclude tillers | |
| Pre-Harvest | Stalk lodging | No. of stalks broken below the primary ear attachment. Exclude leaning tillers | |
| Pre-Harvest | Root lodging | No. of stalks leaning >45° angle from perpendicular. | |
| Pre-Harvest | Stay green | After physiological maturity and when differences among genotypes are evident: Scale 1 (90-100% tissue green)-9 (0-19% tissue green). | |
| Harvest | Grain Yield | Grain yield/plot (Shell weight) | |

When screening for yield improvement a useful statistical measurement approach comprises three components, i.e. modeling spatial autocorrelation of the test field separately for each location, adjusting traits of recombinant DNA events for spatial dependence for each location, and conducting an across location analysis. The first step in modeling spatial autocorrelation is estimating the covariance parameters of the semivariogram. A spherical covariance model is assumed to model the spatial autocorrelation. Because of the size and nature of the trial, it is likely that the spatial autocorrelation may change. Therefore, anisotropy is also assumed along with spherical covariance structure. The following set of equations describes the statistical form of the anisotropic spherical covariance model.

$$C(h;\theta) = vI(h=0) + \sigma^2\left(1 - \frac{3}{2}h + \frac{1}{2}h^3\right)I(h<1)$$

where $I(\cdot)$ is the indicator function $h=\sqrt{\dot{x}^2+\dot{y}^2}$
and $$\dot{x}=[\cos(\rho\pi/180)(x_1-x_2)-\sin(\rho\pi/180)(y_1-y_2)]/\omega_x$$

$$\dot{y}=[\sin(\rho\pi/180)(x_1-x_2)+\cos(\rho\pi/180)(y_1-y_2)]/\omega_y$$

where $s_1=(x_1, y_1)$ are the spatial coordinates of one location and $s_2=(x_2, y_2)$ are the spatial coordinates of the second location. There are 5 covariance parameters, $$\theta=(v,\sigma^2,\rho,\omega_n,\omega_j)$$

where $v$ is the nugget effect, $\sigma^2$ is the partial sill, $\rho$ is a rotation in degrees clockwise from north, $\omega_n$ is a scaling parameter for the minor axis and $\omega_j$ is a scaling parameter for the major axis of an anisotropical ellipse of equal covariance. The five covariance parameters that define the spatial trend will then be estimated by using data from heavily replicated pollinator plots via restricted maximum likelihood approach. In a multi-location field trial, spatial trend are modeled separately for each location.

After obtaining the variance parameters of the model, a variance-covariance structure is generated for the data set to be analyzed. This variance-covariance structure contains spatial information required to adjust yield data for spatial dependence. In this case, a nested model that best represents the treatment and experimental design of the study is used along with the variance-covariance structure to adjust the yield data. During this process the nursery or the seed batch effects can also be modeled and estimated to adjust the yields for any yield parity caused by seed batch differences.

After spatially adjusted data from different locations are generated, all adjusted data is combined and analyzed assuming locations as replications. In this analysis, intra and inter-location variances are combined to estimate the standard error of yield from transgenic plants and control plants. Relative mean comparisons are used to indicate statistically significant yield improvements.

Screening for Water Use Efficiency

An aspect of this invention provides transgenic plants with enhanced yield resulting from enhanced water use efficiency and/or drought tolerance. Described in this example is a high-throughput method for greenhouse selection of transgenic corn plants to wild type corn plants (tested as inbreds or hybrids) for water use efficiency. This selection process imposes 3 drought/re-water cycles on plants over a total period of 15 days after an initial stress free growth period of 11 days. Each cycle consists of 5 days, with no water being applied for the first four days and a water quenching on the 5th day of the cycle. The primary phenotypes analyzed by the selection method are the changes in plant growth rate as determined by height and biomass during a vegetative drought treatment. The hydration status of the shoot tissues following the drought is also measured. The plant heights are measured at three time points. The first is taken just prior to the onset drought when the plant is 11 days old, which is the shoot initial height (SIH). The plant height is also measured halfway throughout the drought/re-water regimen, on day 18 after planting, to give rise to the shoot mid-drought height (SMH). Upon the completion of the final drought cycle on day 26 after planting, the shoot portion of the plant is harvested and measured for a final height, which is the shoot wilt height (SWH) and also measured for shoot wilted biomass (SWM). The shoot is placed in water at 40 degree Celsius in the dark. Three days later, the shoot is weighted to give rise to the shoot turgid weight (STM). After drying in an oven for four days, the shoots are weighted for shoot dry biomass (SDM). The shoot average height (SAH) is the mean plant height across the 3 height measurements. The procedure described above may be adjusted for +/−~one day for each step given the situation.

To correct for slight differences between plants, a size corrected growth value is derived from SIH and SWH. This is the Relative Growth Rate (RGR). Relative Growth Rate (RGR) is calculated for each shoot using the formula [RGR %=(SWH−SIH)/((SWH+SIH)/2)*100]. Relative water content (RWC) is a measurement of how much (%) of the plant was water at harvest. Water Content (RWC) is calculated for each shoot using the formula [RWC %=(SWM−SDM)/(STM−SDM)*100]. Fully watered corn plants of this age run around 98% RWC.

Screening for Growth Under Cold Stress

An aspect of this invention provides transgenic plants with enhanced growth under cold stress, e.g., in an early seedling growth assay. In an early seedling growth assay 3 sets of seeds are assayed. The first set is a group of transgenic seeds from transgenic plants; the second set is negative segregants of the transgenic seed; and the third seed set is seed from two cold tolerant and two cold sensitive wild-type controls. All seeds are treated with a fungicide as indicated above. Seeds are grown in germination paper (12 inch×18 inch pieces of Anchor Paper #SD7606), wetted in a solution of 0.5% KNO3 and 0.1% Thyram. For each paper fifteen seeds are placed on the line evenly spaced such that the radical s will grow toward the same edge. The wet paper is rolled up evenly and tight enough to hold the seeds in place. The roll is secured into place with two large paper clips, one at the top and one at the bottom. The rolls are incubated in a growth chamber at 23 degree C. for three days in a randomized complete block design within an appropriate container. The chamber is set for 65% humidity with no light cycle. For the cold stress treatment the rolls are then incubated in a growth chamber at 12 degree C. for fourteen days. The chamber is set for 65% humidity with no light cycle. For the warm treatment the rolls are incubated at 23 degree C. for an additional two days. After the treatment the germination papers are unrolled and the seeds that did not germinate are discarded. The lengths of the radicle and coleoptile for each seed are measured. A coleoptile sample is collected from six individual kernels of each entry for confirming the expression of recombinant DNA. Statistical differences in the length of radical and shoot during pre-shock and cold shock are used for an estimation of the effect of the cold treatment on corn plants. The analysis is conducted independently for the warm and cold treatments.

Screen for Enhanced Oil, Starch, or Protein Levels in Plant Seeds

Oil levels of plant seeds are determined by low-resolution .sup.1H nuclear magnetic resonance (NMR) (Tiwari et al., JAOCS, 51:104-109 (1974); or Rubel, JAOCS, 71:1057-1062 (1994)). Alternatively, oil, starch and protein levels in seeds are determined by near infrared spectroscopy (NIR).

The following examples illustrate aspects of the invention.

Example 1

This example illustrates the construction of plasmids for transferring recombinant DNA into plant cells which can be regenerated into transgenic plants of this invention. Primers for PCR amplification of protein coding nucleotides of recombinant DNA were designed at or near the start and stop codons of the coding sequence, in order to eliminate most of the 5' and 3' untranslated regions. Each recombinant DNA coding for a protein identified in Table 1 was amplified by PCR prior to insertion into the insertion site of one of the base vectors as referenced in Table 1.

A base plant transformation vector pMON65154 was fabricated for use in preparing recombinant DNA for transformation into corn tissue using GATEWAY™ Destination plant expression vector systems (available from Invitrogen Life Technologies, Carlsbad, Calif.). With reference to the elements described in Table 5 below and SEQ ID NO:9, pMON65154 comprises a selectable marker expression cassette and a template recombinant DNA expression cassette. The marker expression cassette comprises a CaMV 35S promoter operably linked to a gene encoding neomycin phosphotransferase II (nptII) followed by a 3' region of an *Agrobacterium tumefaciens* nopaline synthase gene (nos). The template recombinant DNA expression cassette is positioned tail to tail with the marker expression cassette. The template recombinant DNA expression cassette comprises 5' regulatory DNA including a rice actin 1 promoter, exon and intron, followed by a GATEWAY™ insertion site for recombinant DNA, followed by a 3' region of a potato proteinase inhibitor II (pinII) gene. Once recombinant DNA has been inserted into the insertion site, the plasmid is useful for plant transformation, for example by microprojectile bombardment.

TABLE 5

| FUNCTION | ELEMENT | REFERENCE |
|---|---|---|
| Plant gene of interest expression cassette | Rice actin 1 promoter | U.S. Pat. No. 5,641,876 |
| | Rice actin 1 exon 1, intron 1 enhancer | U.S. Pat. No. 5,641,876 |
| Gene of interest insertion site | AttR1 | GATEWAY ™ Cloning Technology Instruction Manual |
| | CmR gene | GATEWAY ™ Cloning Technology Instruction Manual |
| | ccdA, ccdB genes | GATEWAY ™ Cloning Technology Instruction Manual |
| | attR2 | GATEWAY ™ Cloning Technology Instruction Manual |
| Plant gene of interest expression cassette | Potato pinII 3' region | An et al. (1989) Plant Cell 1: 115-122 |
| Plant selectable marker expression cassette | CaMV 35S promoter | U.S. Pat. No. 5,858,742 |
| | nptII selectable marker | U.S. Pat. No. 5,858,742 |
| | nos 3' region | U.S. Pat. No. 5,858,742 |
| Maintenance in *E. coli* | ColE1 origin of replication | |
| | F1 origin of replication | |
| | Bla ampicillin resistance | | similar base vector plasmid pMON72472 (SEQ ID NO: 10) was constructed for use in *Agrobacterium*-mediated methods of plant transformation similar to pMON65154 except (a) the 5' regulatory DNA in the template recombinant DNA expression cassette was a rice actin promoter and a rice actin intron, (b) left and right T-DNA border sequences from *Agrobacteritm* are added with the right border sequence is located 5' to the rice actin 1 promoter and the left border sequence is located 3' to the 35S promoter and (c) DNA is added to facilitate replication of the plasmid in both *E. coli* and *Agrobacterium tumefaciens*. The DNA added to the plasmid outside of the T-DNA border sequences includes an oriV wide host range origin of DNA replication functional in *Agrobacterium*, a pBR322 origin of replication functional in *E. coli*, and a spectinomycin/stretptomycin resistance gene for selection in both *E. coli* and *Agrobacterium*. pMON74775 is constructed in a base vector essentially the same as pMON72472.

Other base vectors similar to those described above were also constructed including pMON81244 containing a pyruvate orthophosphate dikinase (PPDK) promoter (SEQ ID NO: 11) and a maize DnaK intron (SEQ ID NO: 12) as an enhancer.

Plant Expression Vector for Soybean Transformation

Plasmids for use in transformation of soybean were also prepared. Elements of an exemplary common expression vector plasmid pMON74532 (SEQ ID NO:13) are shown in Table 7 below.

A plasmid vector similar to that described above for soy transformation was constructed for use in *Agrobacterium*-mediated soybean transformation, pMON74537, which contains the *Arabidopsis thaliana* ribulose-1,5-bisphosphate carboxylase (Rubisco) small subunit promoter (SEQ ID NO: 14)

Protein coding segments of recombinant DNA are amplified by PCR prior to insertion into vectors at the insertion site. Primers for PCR amplification are designed at or near the start and stop codons of the coding sequence, in order to eliminate most of the 5' and 3' untranslated regions.

Example 2

This example illustrates plant transformation useful in producing the transgenic corn plants of this invention. Corn plants of a readily transformable line are grown in the greenhouse and ears harvested when the embryos are 1.5 to 2.0 mm in length. Ears are surface sterilized by spraying or soaking the ears in 80% ethanol, followed by air drying. Immature embryos are isolated from individual kernels on surface sterilized ears. Prior to inoculation of maize cells, *Agrobacterium* cells are grown overnight at room temperature. Immature maize embryos are inoculated with *Agrobacterium* shortly after excision, and incubated at room temperature with *Agrobacterium* for 5-20 minutes. Immature embryos are then co-cultured with *Agrobacterium* for 1 to 3 days at 23° C. in the dark. Co-cultured embryos are transferred to selection media and cultured for approximately two weeks to allow embryogenic callus to develop. Embryogenic callus is transferred to culture medium containing 100 mg/L paromomycin and sub-cultured at about two week intervals. Transformants are recovered 6 to 8 weeks after initiation of selection.

Plasmid vectors are prepared cloning DNA identified in Table 1 in the identified base for use in corn transformation to produce transgenic corn plants and seed.

For *Agrobacterium*-mediated transformation of maize callus, immature embryos are cultured for approximately 8-21 days after excision to allow callus to develop. Callus is then incubated for about 30 minutes at room temperature with the *Agrobacterium* suspension, followed by removal of the liquid by aspiration. The callus and *Agrobacterium* are co-cultured without selection for 3-6 days followed by selection on paromomycin for approximately 6 weeks, with biweekly transfers to fresh media, and paromomycin resistant callus identified as containing the recombinant DNA in an expression cassette.

TABLE 7

| Function | Element | Reference |
|---|---|---|
| Agro transformation | B-ARGtu.right border | Depicker, A. et al (1982) Mol Appl Genet 1: 561-573 |
| Antibiotic resistance | CR-Ec.aadA-SPC/STR | |
| Repressor of primers from the ColE1 plasmid | CR-Ec.rop | |
| Origin of replication | OR-Ec.oriV-RK2 | |
| Agro transformation | B-ARGtu.left border | Barker, R. F. et al (1983) Plant Mol Biol 2: 335-350 |
| Plant selectable marker expression cassette | Promoter with intron and 5'UTR of *Arabidopsis* act 7 gene (AtAct7) | McDowell et al. (1996) Plant Physiol. 111: 699-711. |
| | 5' UTR of *Arabidopsis* act 7 gene | |
| | Intron in 5'UTR of AtAct7 | |
| | Transit peptide region of *Arabidopsis* EPSPS | Klee, H. J. et al (1987) MGG 210: 437-442 |
| | Synthetic CP4 coding region with dicot preferred codon usage | |
| | A 3' UTR of the nopaline synthase gene of *Agrobacterium tumefaciens* Ti plasmid | U.S. Pat. No. 5,858,742 |
| Plant gene of interest expression cassette | Promoter for 35S RNA from CaMV containing a duplication of the −90 to −350 region | U.S. Pat. No. 5,322,938 |
| | Gene of interest insertion site | |
| | Cotton E6 3' end | GenBank accession U30508 |

For transformation by microprojectile bombardment, immature maize embryos are isolated and cultured 3-4 days prior to bombardment. Prior to microprojectile bombardment, a suspension of gold particles is prepared onto which the desired recombinant DNA expression cassettes are precipitated. DNA is introduced into maize cells as described in U.S. Pat. Nos. 5,550,318 and 6,399,861 using the electric discharge particle acceleration gene delivery device. Following microprojectile bombardment, tissue is cultured in the dark at 27 degrees C.

To regenerate transgenic corn plants transgenic callus resulting from transformation is placed on media to initiate shoot development in plantlets which are transferred to potting soil for initial growth in a growth chamber at 26 degrees C. followed by a mist bench before transplanting to 5 inch pots where plants are grown to maturity. The plants are self fertilized and seed is harvested for screening as seed, seedlings or progeny R2 plants or hybrids, e.g., for yield trials in the screens indicated above.

Example 3

This example further illustrates the production and identification of transgenic seed for transgenic corn having an enhanced agronomic trait, i.e. enhanced nitrogen use efficiency, increased yield, enhanced water use efficiency, enhanced tolerance to cold and/or improved seed compositions as compared to control plants. Transgenic corn seed and plants comprising recombinant DNA from each of the genes cloned in one of base vectors as identified in Table 1 are prepared by transformation. Many transgenic events which survive to fertile transgenic plants that produce seeds and progeny plants will not exhibit an enhanced agronomic trait. The transgenic plants and seeds having enhanced agronomic traits of this invention are identified by screening for nitrogen use efficiency, yield, water use efficiency, and cold tolerance. Transgenic plants providing seeds with improved seed compositions are identified by analyzing for seed compositions including protein, oil and starch levels.

A. Enhanced Nitrogen Use Efficiency

The transgenic plants with enhanced nitrogen use efficiency provided by this invention were selected through the selection process according to the standard procedure described above and the performance of these transgenic plants are shown in Table 8 below.

Yield

The transgenic plants with enhanced yield provided by this invention were selected through the selection process according to the standard procedure described above and the performance of these transgenic plants are shown in Tables 9 and 10 below indicating the change in corn yield measured in bushels per acre.

TABLE 9

| Event | Broad Acre Yield | | High density Yield |
|---|---|---|---|
| | Year 1 | Year 2 | |
| 24861 | 3.9 | −2.22 | −5.3 |
| 24862 | 0.51 | −1.86 | 2.8 |
| 24870 | 2.33 | 5.41 | 7.81 |
| 24874 | 5.21 | 2.61 | 8.21 |
| 26391 | 1.13 | −3.59 | 5.1 |

TABLE 10

| Event | Delta | Percent change | P-value |
|---|---|---|---|
| ZM_M81660 | −6.20 | −3.47 | 0.05 |
| ZM_M81671 | −21.99 | −12.32 | 0.00 |
| ZM_M81675 | −23.94 | −13.41 | 0.00 |
| ZM_M81677 | −3.71 | −2.08 | 0.23 |
| ZM_M81682 | −5.58 | −3.12 | 0.11 |
| ZM_M81684 | −14.72 | −8.25 | 0.00 |
| ZM_M81687 | 4.83 | 2.71 | 0.13 |
| ZM_M81688 | −14.64 | −8.20 | 0.00 |

Water Use Efficiency

The transgenic plants with enhanced water use efficiency provided by this invention were selected through the selection process according to the standard procedure described above and the performance of these transgenic plants are shown in Table 11 below.

TABLE 8

| Event ID | Leaf chlorophyll area | | | | Leaf chlorophyll | | | | Shoot fresh mass | | | |
|---|---|---|---|---|---|---|---|---|---|---|---|---|
| | Percent change | Mean | Mean of controls | P-value | Percent change | Mean | Mean of controls | P-value | Percent change | Mean | Mean of controls | P-value |
| ZM_M24857 | −1 | 5366.5 | 5430 | 0.75 | 2 | 27.8 | 27.3 | 0.48 | −3 | 51.6 | 53.4 | 0.31 |
| ZM_M24857 | −24 | 4150.6 | 5430 | 0.00 | −8 | 25.1 | 27.3 | 0.01 | −33 | 36 | 53.4 | 0.00 |
| ZM_M24861 | 12 | 3811.5 | 3397.7 | 0.00 | 7 | 25.2 | 23.5 | 0.02 | 8 | 31.2 | 28.8 | 0.02 |
| ZM_M24861 | 0 | 5430.4 | 5430 | 1.00 | 6 | 28.9 | 27.3 | 0.04 | 1 | 54.2 | 53.4 | 0.66 |
| ZM_M24870 | −2 | 5347.4 | 5430 | 0.68 | −1 | 27 | 27.3 | 0.72 | −9 | 48.9 | 53.4 | 0.01 |
| ZM_M24870 | −3 | 5268.1 | 5430 | 0.41 | 5 | 28.6 | 27.3 | 0.10 | −5 | 50.8 | 53.4 | 0.14 |
| ZM_M24873 | −7 | 5023.8 | 5430 | 0.04 | −9 | 24.8 | 27.3 | 0.00 | −18 | 43.7 | 53.4 | 0.00 |
| ZM_M24873 | −5 | 5159.9 | 5430 | 0.17 | 4 | 28.4 | 27.3 | 0.15 | −11 | 47.7 | 53.4 | 0.00 |
| ZM_M24874 | −3 | 5289.5 | 5430 | 0.48 | 2 | 27.8 | 27.3 | 0.50 | −3 | 51.9 | 53.4 | 0.40 |
| ZM_M24874 | −2 | 5319.7 | 5430 | 0.58 | 1 | 27.5 | 27.3 | 0.77 | −2 | 52.4 | 53.4 | 0.58 |
| ZM_M26391 | −9 | 4914.4 | 5430 | 0.01 | 0 | 27.2 | 27.3 | 0.91 | −2 | 52.5 | 53.4 | 0.60 |
| ZM_M26391 | −3 | 5273.7 | 5430 | 0.43 | 3 | 28 | 27.3 | 0.35 | −2 | 52.2 | 53.4 | 0.48 |

TABLE 11

| Event | % SAH | P value SAH | % RGR | P value RGR | % SDM | P value SDM | % RWC | P value RWC |
|---|---|---|---|---|---|---|---|---|
| ZM_M24857 | 1.02 | 0.02 | 1.63 | 0.05 | 3.29 | 0.02 | 1.52 | 0.16 |
| ZM_M24857 | −4.22 | 0.00 | 10.66 | 0.00 | −4.33 | 0.00 | 4.59 | 0.00 |
| ZM_M24861 | −1.53 | 0.00 | 2.09 | 0.01 | 2.88 | 0.03 | 2.65 | 0.02 |
| ZM_M24861 | −2.75 | 0.00 | 5.85 | 0.00 | 0.33 | 0.81 | 4.86 | 0.00 |
| ZM_M24862 | −0.56 | 0.20 | −5.05 | 0.00 | 3.33 | 0.01 | −3.04 | 0.01 |
| ZM_M24870 | −3.17 | 0.00 | 8.47 | 0.00 | −4.36 | 0.00 | −1.29 | 0.23 |
| ZM_M24870 | 0.29 | 0.50 | 1.24 | 0.12 | −0.36 | 0.79 | −2.05 | 0.06 |
| ZM_M24873 | −3.54 | 0.00 | 6.88 | 0.00 | −4.88 | 0.00 | 1.30 | 0.25 |
| ZM_M24873 | −4.61 | 0.00 | 10.51 | 0.00 | −3.08 | 0.02 | −1.92 | 0.08 |
| ZM_M24874 | 0.00 | 1.00 | −3.57 | 0.00 | 2.96 | 0.03 | −2.45 | 0.03 |
| ZM_M24874 | −1.96 | 0.00 | 2.17 | 0.01 | −0.60 | 0.66 | 1.16 | 0.31 |
| ZM_M26391 | −2.18 | 0.00 | 4.02 | 0.00 | −1.01 | 0.45 | −0.11 | 0.92 |
| ZM_M26391 | 0.76 | 0.08 | −4.44 | 0.00 | 2.77 | 0.04 | 2.67 | 0.01 |

Cold Tolerance

The transgenic plants with enhanced cold tolerance provided by this invention were selected through the selection process according to the standard procedure described above and the performance of the early seedling growth of these transgenic plants are shown in Table 12 below.

Improved Seed Composition

The transgenic plants with improved seed composition provided by this invention were selected through the selection process according to the standard procedure described above and the performance of these transgenic plants are shown in Tables 13-5.

TABLE 12

| | Root length | | | | Shoot length | | | | Seedling length | | | |
|---|---|---|---|---|---|---|---|---|---|---|---|---|
| Event ID | Percent change | Mean | Mean of controls | P-value | Percent change | Mean | Mean of controls | P-value | Percent change | Mean | Mean of controls | P-value |
| ZM_M24857 | 23 | 14.81 | 12.07 | 0.01 | 15 | 10.07 | 8.77 | 0.02 | 19 | 24.89 | 20.84 | 0.01 |
| ZM_M24857 | 18 | 14.1 | 11.97 | 0.01 | 6 | 10.35 | 9.72 | 0.13 | 13 | 24.45 | 21.69 | 0.02 |
| ZM_M24857 | 9 | 13.69 | 12.56 | 0.03 | 12 | 9.13 | 8.17 | 0.01 | 10 | 22.81 | 20.74 | 0.01 |
| ZM_M24857 | 14 | 13.68 | 11.97 | 0.04 | 10 | 10.66 | 9.72 | 0.02 | 12 | 24.33 | 21.69 | 0.03 |
| ZM_M24857 | −11 | 10.12 | 11.39 | 0.10 | −3 | 8.24 | 8.48 | 0.64 | −8 | 18.36 | 19.87 | 0.21 |
| ZM_M24861 | 5 | 13.43 | 12.79 | 0.32 | −10 | 7.71 | 8.58 | 0.07 | −1 | 21.13 | 21.37 | 0.82 |
| ZM_M24861 | 4 | 12.4 | 11.97 | 0.61 | −3 | 9.43 | 9.72 | 0.48 | 1 | 21.83 | 21.69 | 0.91 |
| ZM_M24861 | −10 | 10.15 | 11.32 | 0.11 | −12 | 8.96 | 10.22 | 0.01 | −11 | 19.11 | 21.54 | 0.04 |
| ZM_M24862 | −9 | 10.32 | 11.32 | 0.17 | −7 | 9.47 | 10.22 | 0.14 | −8 | 19.79 | 21.54 | 0.13 |
| ZM_M24870 | 14 | 13.65 | 11.97 | 0.05 | 7 | 10.43 | 9.72 | 0.09 | 11 | 24.09 | 21.69 | 0.04 |
| ZM_M24870 | −2 | 12.28 | 12.56 | 0.59 | 1 | 8.29 | 8.17 | 0.75 | −1 | 20.58 | 20.74 | 0.83 |
| ZM_M24870 | 11 | 13.31 | 11.97 | 0.11 | 4 | 10.11 | 9.72 | 0.34 | 8 | 23.42 | 21.69 | 0.14 |
| ZM_M24870 | 0 | 10.46 | 10.45 | 0.98 | 2 | 8.08 | 7.96 | 0.82 | 1 | 18.55 | 18.41 | 0.89 |
| ZM_M24873 | 10 | 13.2 | 11.97 | 0.14 | 5 | 10.2 | 9.72 | 0.25 | 8 | 23.39 | 21.69 | 0.15 |
| ZM_M24873 | −8 | 11.83 | 12.79 | 0.13 | −10 | 7.75 | 8.58 | 0.08 | −8 | 19.58 | 21.37 | 0.08 |
| ZM_M24873 | 17 | 14.06 | 11.97 | 0.01 | 16 | 11.3 | 9.72 | 0.00 | 17 | 25.36 | 21.69 | 0.00 |
| ZM_M24873 | −7 | 11.74 | 12.56 | 0.11 | 0 | 8.16 | 8.17 | 0.98 | −4 | 19.91 | 20.74 | 0.28 |
| ZM_M24874 | −13 | 11.15 | 12.79 | 0.01 | −19 | 6.92 | 8.58 | 0.00 | −15 | 18.07 | 21.37 | 0.00 |
| ZM_M24874 | 13 | 13.52 | 11.97 | 0.07 | 8 | 10.54 | 9.72 | 0.05 | 11 | 24.06 | 21.69 | 0.05 |
| ZM_M24874 | −10 | 11.33 | 12.56 | 0.02 | −4 | 7.87 | 8.17 | 0.43 | −7 | 19.21 | 20.74 | 0.05 |
| ZM_M24874 | 2 | 12.25 | 11.97 | 0.74 | 7 | 10.39 | 9.72 | 0.11 | 4 | 22.64 | 21.69 | 0.42 |
| ZM_M26391 | 23 | 14.72 | 11.97 | 0.00 | 17 | 11.37 | 9.72 | 0.00 | 20 | 26.08 | 21.69 | 0.00 |
| ZM_M26391 | −6 | 11.82 | 12.56 | 0.15 | 7 | 8.72 | 8.17 | 0.16 | −1 | 20.54 | 20.74 | 0.80 |
| ZM_M26391 | −23 | 8.09 | 10.45 | 0.00 | −14 | 6.88 | 7.96 | 0.04 | −19 | 14.97 | 18.41 | 0.00 |
| ZM_M26391 | 9 | 13.01 | 11.97 | 0.21 | 10 | 10.72 | 9.72 | 0.02 | 9 | 23.72 | 21.69 | 0.09 |

TABLE 13

| | | Oil | | | | | | |
|---|---|---|---|---|---|---|---|---|
| | | | Y2 Hybrid Data | | | | Y1 Hybrid Data | |
| Event | Construct | Mean | Control mean | Percent change | Delta | P-value | Delta | P-value |
| ZM_M24870 | PMON68392 | 4.48 | 4.29 | 4.28 | 0.18 | 0.04 | 0.14 | 0.15 |
| ZM_S368719 | PMON74775 | 4.43 | 4.12 | 7.38 | 0.30 | 0.00 | #N/A | #N/A |
| ZM_S69656 | PMON74775 | 4.36 | 4.12 | 5.59 | 0.23 | 0.03 | 0.33 | 0.02 |

TABLE 14

| | | Oil | | | |
|---|---|---|---|---|---|
| Event | Construct | Mean | Mean control | Delta | P-value |
| ZM_M92534 | PMON84131 | 4.94 | 4.51 | 0.42 | 0.00 |
| ZM_M91731 | PMON84131 | 4.90 | 4.51 | 0.38 | 0.01 |
| ZM_M92532 | PMON84131 | 4.87 | 4.51 | 0.35 | 0.02 |

TABLE 15

| | | Protein | |
|---|---|---|---|
| Event | Construct | Protein delta | Protein p-value |
| ZM_M24870 | PMON68392 | 0.44 | 0.02 |
| ZM_S68719 | PMON74775 | 0.35 | 0.12 |
| ZM_S69656 | PMON74775 | 0.21 | 0.35 |

Example 4

This example illustrate transgenic plants with enhanced traits through combinations. As illustrated in the Example 3, transgenic plants with enhanced agronomic traits are generated employing the recombinant DNA from each of the genes identified in Table 1. To produce further enhancement of agronomic traits in transgenic plants, the genes of Table 1 are combined with one or more additional genes that enhance agronomic traits to generate a transgenic plant with greater enhancement in one or more agronomic traits than either gene alone. This combination is achieved through either through transformation or breeding. The following example illustrates this principle. A transgenic maize plant stably transformed with a construct, pMON74923, containing the *Zea mays* phytochrome B (phyB) gene (SEQ ID NO: 15) under the control of a maize aldolase (FDA) promoter (U.S. patent application Ser. No. 09/757,089) was crossed with a transgenic maize plant stably transformed with pMON68392. The cross demonstrated an increased yield (bu./a) of 7.2% compared to the maize plant containing the phyB gene alone (2.4%).

Example 5

Soybean Plant Transformation

This example illustrates plant transformation useful in producing the transgenic soybean plants of this invention and the production and identification of transgenic seed for transgenic soybean having an enhanced agronomic trait, i.e. enhanced nitrogen use efficiency, enhanced yield, enhanced water use efficiency, enhanced growth under cold stress, and/or enhanced seed oil, protein and/or starch levels as compared to control plants. For *Agrobacterium* mediated transformation, soybean seeds are germinated overnight and the meristem explants excised. The meristems and the explants are placed in a wounding vessel. Soybean explants and induced *Agrobacterium* cells from a strain containing plasmid DNA with the gene of interest cassette and a plant selectable marker cassette are mixed no later than 14 hours from the time of initiation of seed germination and wounded using sonication. Following wounding, explants are placed in co-culture for 2-5 days at which point they are transferred to selection media for 6-8 weeks to allow selection and growth of transgenic shoots. Trait positive shoots are harvested approximately 6-8 weeks post bombardment and placed into selective rooting media for 2-3 weeks. Shoots producing roots are transferred to the greenhouse and potted in soil. Shoots that remain healthy on selection, but do not produce roots are transferred to non-selective rooting media for an additional two weeks. Roots from any shoots that produce roots off selection are tested for expression of the plant selectable marker before they are transferred to the greenhouse and potted in soil.

Example 6

This example further illustrates the production and identification of transgenic seed for transgenic soybean having an enhanced agronomic trait, i.e. enhanced nitrogen use efficiency, increased yield, enhanced water use efficiency, enhanced growth under cold stress, and/or improved seed compositions as compared to control plants. Transgenic soybean seed and plants comprising recombinant DNA from each of the genes cloned in one of base vectors as identified in Table 1 are prepared by transformation. Many transgenic events which survive to fertile transgenic plants that produce seeds and progeny plants will not exhibit an enhanced agronomic trait. The transgenic plants and seeds having enhanced agronomic traits of this invention are identified by screening for nitrogen use efficiency, yield, water use efficiency, and cold tolerance. Transgenic plants providing seeds with improved seed compositions are identified by analyzing for seed compositions including protein, oil and starch levels.

What is claimed is:

1. A corn plant cell with stably integrated, recombinant DNA comprising a promoter that is functional in plant cells and that is operably linked to DNA that encodes a protein comprising SEQ ID NO:5; wherein a plant comprising said plant cell exhibits an increased yield of at least 0.51 bushels per acre as compared to a control plant that does not have said recombinant DNA.

2. The corn plant cell of claim 1 further comprising DNA expressing a protein that provides tolerance from exposure to an herbicide applied at levels that are lethal to a wild type of said plant cell.

3. The corn plant cell of claim 2 wherein said herbicide is a glyphosate, dicamba, or glufosinate compound.

4. A corn plant transformed with recombinant DNA comprising a promoter that is functional in plant cells and that is operably linked to DNA that encodes a protein comprising SEQ ID NO:5; wherein said plant exhibits an increased yield of at least 0.51 bushels per acre as compared to control plants that do not have said recombinant DNA.

5. The corn plant of claim 4 which is homozygous for said recombinant DNA.

6. A transgenic corn seed of the plant of claim 4, wherein the seed comprises said recombinant DNA.

7. Non-natural, transgenic corn seed of claim 6 wherein said seed can produce corn plants that are resistant to disease from the Mal de Rio Cuarto virus or the *Puccina sorghi* fungus or both.

8. A transgenic pollen grain comprising a haploid gamete of the corn plant cell of claim 1, wherein said gamete comprises said recombinant DNA.

9. A corn plant cell with stably integrated, recombinant DNA comprising a promoter that is functional in plant cells and that is operably linked to DNA that encodes a protein comprising SEQ ID NO:5; wherein a plant comprising said plant cell exhibits increased kernel weight, increased kernel size, or increased ear size as compared to a control plant that does not have said recombinant DNA.

10. The corn plant cell of claim 9, further comprising DNA expressing a protein that provides tolerance from exposure to an herbicide applied at levels that are lethal to a wild type of said plant cell.

11. The corn plant cell of claim 10, wherein said herbicide is a glyphosate, dicamba, or glufosinate compound.

12. A transgenic corn seed derived from the plant cell of claim 9, wherein the seed comprises the stably integrated, recombinant DNA.

* * * * *